United States Patent
Pepinsky et al.

(10) Patent No.: US 6,962,978 B2
(45) Date of Patent: Nov. 8, 2005

(54) POLYMER CONJUGATES OF INTERFERON BETA-1A AND USES

(75) Inventors: Blake Pepinsky, Arlington, MA (US); Laura Runkel, Cambridge, MA (US); Margot Brickelmaier, Boxford, MA (US); Adrian Whitty, Hopkinton, MA (US); Paula Hochman, Newton, MA (US)

(73) Assignee: Biogen, Inc., Cambridge, MA (US)

( * ) Notice: Subject to any disclaimer, the term of this patent is extended or adjusted under 35 U.S.C. 154(b) by 283 days.

(21) Appl. No.: 09/832,658

(22) Filed: Apr. 11, 2001

(65) Prior Publication Data

US 2003/0021765 A1 Jan. 30, 2003

Related U.S. Application Data

(63) Continuation of application No. PCT/US99/24201, filed on Oct. 15, 1999.
(60) Provisional application No. 60/104,572, filed on Oct. 16, 1998, and provisional application No. 60/120,161, filed on Feb. 16, 1999.

(51) Int. Cl.[7] ............... C07K 14/52; C07K 14/555; A61K 38/21
(52) U.S. Cl. ............... 530/351; 530/395; 530/402; 514/12; 424/85.6; 930/142
(58) Field of Search ............... 530/351, 395, 530/402; 514/12; 424/85.6; 930/142

(56) References Cited

U.S. PATENT DOCUMENTS

| | | | |
|---|---|---|---|
| 4,179,337 A | 12/1979 | Davis et al. | |
| 4,751,077 A | 6/1988 | Bell et al. | |
| 4,894,226 A | 1/1990 | Aldwin et al. | |
| 4,917,888 A | 4/1990 | Katre et al. | |
| 5,109,120 A | 4/1992 | Ueno et al. | |
| 5,116,964 A | * 5/1992 | Capon et al. | 536/27 |
| 5,252,714 A | 10/1993 | Harris et al. | |
| 5,281,698 A | 1/1994 | Nitecki | |
| 5,286,637 A | 2/1994 | Veronese et al. | |
| 5,359,030 A | 10/1994 | Ekwuribe | |
| 5,382,657 A | 1/1995 | Karasiewicz et al. | |
| 5,529,915 A | 6/1996 | Phillips et al. | |
| 5,643,575 A | 7/1997 | Martinez et al. | |
| 5,681,811 A | 10/1997 | Ekwuribe | |
| 5,702,717 A | 12/1997 | Cha et al. | |
| 5,711,944 A | 1/1998 | Gilbert et al. | |
| 5,738,846 A | 4/1998 | Greenwald et al. | |
| 5,792,834 A | 8/1998 | Hakimi et al. | |
| 5,824,784 A | 10/1998 | Kinstler et al. | |
| 5,874,075 A | 2/1999 | Collins et al. | |
| 5,965,119 A | 10/1999 | Greenwald et al. | |
| 5,985,265 A | 11/1999 | Kinstler et al. | |
| 5,990,237 A | 11/1999 | Bentley et al. | |
| 6,180,095 B1 | 1/2001 | Greenwald et al. | |
| 2001/0011115 A1 | 8/2001 | Harris et al. | |

FOREIGN PATENT DOCUMENTS

| | | |
|---|---|---|
| EP | 0 154 316 | 9/1989 |
| EP | 0 229 108 | 12/1990 |
| WO | WO 87/00056 | 1/1987 |
| WO | WO 95/13090 | 5/1995 |
| WO | WO 97/18832 | 11/1995 |
| WO | WO 96/11953 | 4/1996 |
| WO | WO 99/32134 | 12/1997 |
| WO | WO 98/48840 | 11/1998 |
| WO | WO 99/32139 | 7/1999 |
| WO | WO 99/32140 | 7/1999 |
| WO | WO 99/55377 | 11/1999 |
| WO | WO 01/46291 | 6/2001 |

OTHER PUBLICATIONS

GenBank Accession No.: E00029 (Sep. 29, 1997).
Karpusas et al. (1997). *Proc. Natl. Acad. Sci. USA* 94: 11813–11818.
Runkel et al. (1998). *Pharm. Res. 15*: 641–649.
International Search Report for PCT/US99/24201 mailed Jul. 7, 2000.

* cited by examiner

*Primary Examiner*—Gary Kunz
*Assistant Examiner*—Fozia Hamud
(74) *Attorney, Agent, or Firm*—Foley & Hoag LLP; Isabelle M. Clauss

(57) ABSTRACT

An interferon beta polypeptide comprising interferon-beta 1a coupled to a polymer containing a polyalkylene glycol moiety wherein the interferon-beta-1a and the polyalkylene glycol moiety are arranged such that the interferon-beta-1a has an enhanced activity relative to another therapeutic form of interferon beta (interferon-beta-1b) and exhibits no decrease in activity as compared to non-conjugated interferon-beta-1a. The conjugates of the invention are usefully employed in therapeutic as well as non-therapeutic, e.g., diagnostic, applications.

24 Claims, 11 Drawing Sheets

```
  1 TCCGGGGGCC ATCATCATCA TCATCATAGC TCCGGAGACG ATGATGACAA GATGAGCTAC
    AGGCCCCCGG TAGTAGTAGT AGTAGTATCG AGGCCTCTGC TACTACTGTT CTACTCGATG
  1►SerGlyGlyH IsHIsHIsHI sHIsHIsSer SerGlyAspA spAspAspLy sMetSerTyr

61 AACTTGCTTG GATTCCTACA AAGAAGCAGC AATTTTCAGT GTCAGAAGCT CCTGTGGCAA
    TTGAACGAAC CTAAGGATGT TTCTTCGTCG TTAAAAGTCA CAGTCTTCGA GGACACCGTT
 21►AsnLeuLeuG lyPheLeuGl nArgSerSer AsnPheGlnC ysGlnLysLe uLeuTrpGln

121 TTGAATGGGA GGCTTGAATA CTGCCTCAAG GACAGGATGA ACTTTGACAT CCCTGAGGAG
    AACTTACCCT CCGAACTTAT GACGGAGTTC CTGTCCTACT TGAAACTGTA GGGACTCCTC
 41►LeuAsnGlyA rgLeuGluTy rCysLeuLys AspArgMetA snPheAspIl eProGluGlu

181 ATTAAGCAGC TGCAGCAGTT CCAGAAGGAG GACGCCGCAT TGACCATCTA TGAGATGCTC
    TAATTCGTCG ACGTCGTCAA GGTCTTCCTC CTGCGGCGTA ACTGGTAGAT ACTCTACGAG
 61►IleLysGlnL euGlnGlnPh eGlnLysGlu AspAlaAlaL euThrIleTy rGluMetLeu

241 CAGAACATCT TTGCTATTTT CAGACAAGAT TCATCTAGCA CTGGCTGGAA TGAGACTATT
    GTCTTGTAGA AACGATAAAA GTCTGTTCTA AGTAGATCGT GACCGACCTT ACTCTGATAA
 81►GlnAsnIleP heAlaIlePh eArgGlnAsp SerSerSerT hrGlyTrpAs nGluThrIle

301 GTTGAGAACC TCCTGGCTAA TGTCTATCAT CAGATAAACC ATCTGAAGAC AGTCCTGGAA
    CAACTCTTGG AGGACCGATT ACAGATAGTA GTCTATTTGG TAGACTTCTG TCAGGACCTT
101►ValGluAsnL euLeuAlaAs nValTyrHis GlnIleAsnH isLeuLysTh rValLeuGlu

361 GAAAAACTGG AGAAAGAAGA TTTCACCAGG GGAAAACTCA TGAGCAGTCT GCACCTGAAA
    CTTTTTGACC TCTTTCTTCT AAAGTGGTCC CCTTTTGAGT ACTCGTCAGA CGTGGACTTT
121►GluLysLeuG luLysGluAs pPheThrArg GlyLysLeuM etSerSerLe uHisLeuLys

421 AGATATTATG GGAGGATTCT GCATTACCTG AAGGCCAAGG AGTACAGTCA CTGTGCCTGG
    TCTATAATAC CCTCCTAAGA CGTAATGGAC TTCCGGTTCC TCATGTCAGT GACACGGACC
141►ArgTyrTyrG lyArgIleLe uHisTyrLeu LysAlaLysG luTyrSerHi sCysAlaTrp

481 ACCATAGTCA GAGTGGAAAT CCTAAGGAAC TTTTACTTCA TTAACAGACT TACAGGTTAC
    TGGTATCAGT CTCACCTTTA GGATTCCTTG AAAATGAAGT AATTGTCTGA ATGTCCAATG
161►ThrIleValA rgValGluIl eLeuArgAsn PheTyrPheI leAsnArgLe uThrGlyTyr

541 CTCCGAAAC
    GAGGCTTTG
181►LeuArgAsn
```

FIG. 10

SEQUENCE LISTING

<160> NUMBER OF SEQ ID NOS: 29

<210> SEQ ID NO 1
<211> LENGTH: 549
<212> TYPE: DNA
<213> ORGANISM: murine

<400> SEQUENCE: 1

```
tccgggggcc atcatcatca tcatcatagc tccggagacg atgatgacaa gatgagctac      60
aacttgcttg gattcctaca aagaagcagc aattttcagt gtcagaagct cctgtggcaa     120
ttgaatggga ggcttgaata ctgcctcaag gacaggatga actttgacat ccctgaggag     180
attaagcagc tgcagcagtt ccagaaggag gacgccgcat tgaccatcta tgagatgctc     240
cagaacatct ttgctatttt cagacaagat tcatctagca ctggctggaa tgagactatt     300
gttgagaacc tcctggctaa tgtctatcat cagataaaac atctgaagac agtcctggaa     360
gaaaaactgg agaaagaaga tttcaccagg ggaaaactca tgagcagtct gcacctgaaa     420
agatattatg ggaggattct gcattacctg aaggccaagg agtacagtca ctgtgcctgg     480
accatagtca gagtggaaat cctaaggaac ttttacttca ttaacagact tacaggttac     540
ctccgaaac                                                             549
```

<210> SEQ ID NO 2
<211> LENGTH: 183
<212> TYPE: PRT
<213> ORGANISM: murine

<400> SEQUENCE: 2

Ser Gly Gly His His His His His His Ser Ser Gly Asp Asp Asp Asp
1               5                   10                  15

Lys Met Ser Tyr Asn Leu Leu Gly Phe Leu Gln Arg Ser Ser Asn Phe
            20                  25                  30

Gln Cys Gln Lys Leu Leu Trp Gln Leu Asn Gly Arg Leu Glu Tyr Cys
        35                  40                  45

-continued

```
Leu Lys Asp Arg Met Asn Phe Asp Ile Pro Glu Glu Ile Lys Gln Leu
 50                  55                  60

Gln Gln Phe Gln Lys Glu Asp Ala Ala Leu Thr Ile Tyr Glu Met Leu
 65                  70                  75                  80

Gln Asn Ile Phe Ala Ile Phe Arg Gln Asp Ser Ser Thr Gly Trp
                 85                  90                  95

Asn Glu Thr Ile Val Glu Asn Leu Leu Ala Asn Val Tyr His Gln Ile
                100                 105                 110

Asn His Leu Lys Thr Val Leu Glu Glu Lys Leu Glu Lys Glu Asp Phe
            115                 120                 125

Thr Arg Gly Lys Leu Met Ser Ser Leu His Leu Lys Arg Tyr Tyr Gly
130                 135                 140

Arg Ile Leu His Tyr Leu Lys Ala Lys Glu Tyr Ser His Cys Ala Trp
145                 150                 155                 160

Thr Ile Val Arg Val Glu Ile Leu Arg Asn Phe Tyr Phe Ile Asn Arg
                165                 170                 175

Leu Thr Gly Tyr Leu Arg Asn
                180
```

```
<210> SEQ ID NO 3
<211> LENGTH: 60
<212> TYPE: DNA
<213> ORGANISM: human

<400> SEQUENCE: 3
ttctccggag acgatgatga caagatgagc tacaacttgc ttggattcct acaaagaagc    60

<210> SEQ ID NO 4
<211> LENGTH: 39
<212> TYPE: DNA
<213> ORGANISM: human

<400> SEQUENCE: 4
gccgctcgag ttatcagttt cggaggtaac ctgtaagtc                           39

<210> SEQ ID NO 5
<211> LENGTH: 35
<212> TYPE: DNA
<213> ORGANISM: human

<400> SEQUENCE: 5
agcttccggg ggccatcatc atcatcatca tagct                               35

<210> SEQ ID NO 6
<211> LENGTH: 35
<212> TYPE: DNA
<213> ORGANISM: human

<400> SEQUENCE: 6
ccggagctat gatgatgatg atgatggccc ccgga                               35

<210> SEQ ID NO 7
<211> LENGTH: 87
<212> TYPE: DNA
<213> ORGANISM: human

<400> SEQUENCE: 7
ccggagacga tgatgacaag atggcttacg ccgctcttgg agccctacaa gcttctagca    60
attttcagtg tcagaagctc ctgtggc                                        87
```

<210> SEQ ID NO 8
<211> LENGTH: 60
<212> TYPE: DNA
<213> ORGANISM: human

<400> SEQUENCE: 8
gatctagcaa tgctgcctgt gctgccctcc tggctgcctt gaatgggagg cttgaatact    60

<210> SEQ ID NO 9
<211> LENGTH: 52
<212> TYPE: DNA
<213> ORGANISM: human

<400> SEQUENCE: 9
gcctcaagga caggatgaac tttgacatcc ctgaggagat taagcagctg ca    52

<210> SEQ ID NO 10
<211> LENGTH: 76
<212> TYPE: DNA
<213> ORGANISM: human

<400> SEQUENCE: 10
aattgaatgg gagggctgca gcttgcgctg cagacaggat gaactttgac atccctgagg    60
agattaagca gctgca    76

<210> SEQ ID NO 11
<211> LENGTH: 76
<212> TYPE: DNA
<213> ORGANISM: human

<400> SEQUENCE: 11
aattgaatgg gaggcttgaa tactgcctca aggacagggc tgcatttgct atccctgcag    60
agattaagca gctgca    76

<210> SEQ ID NO 12
<211> LENGTH: 51
<212> TYPE: DNA
<213> ORGANISM: human

<400> SEQUENCE: 12
aattgaatgg gaggcttgaa tactgcctca aggacaggat gaactttgac a    51

<210> SEQ ID NO 13
<211> LENGTH: 43
<212> TYPE: DNA
<213> ORGANISM: human

<400> SEQUENCE: 13
tccctgagga gattgctgca gctgcagctt tcgctgcagc tga    43

<210> SEQ ID NO 14
<211> LENGTH: 78
<212> TYPE: DNA
<213> ORGANISM: human

<400> SEQUENCE: 14
cgccgcgttg accatctatg agatgctcgc taacatcgct agcattttca gacaagattc    60
atctagcact ggctggaa    78

```
<210> SEQ ID NO 15
<211> LENGTH: 78
<212> TYPE: DNA
<213> ORGANISM: human

<400> SEQUENCE: 15
cgccgcattg accatctatg agatgctcca gaacatcttt gctattttcg ctgcagcttc    60
atctagcact ggctggaa                                                  78

<210> SEQ ID NO 16
<211> LENGTH: 72
<212> TYPE: DNA
<213> ORGANISM: human

<400> SEQUENCE: 16
ggaatgcttc aattgttgct gcactcctga gcaatgtcta tcatcagata aaccatctga    60
agacagttct ag                                                        72

<210> SEQ ID NO 17
<211> LENGTH: 72
<212> TYPE: DNA
<213> ORGANISM: human

<400> SEQUENCE: 17
ggaatgagac cattgttgag aacctcctgg ctaatgtcgc tcatcagata gcacatctgg    60
ctgcagttct ag                                                        72

<210> SEQ ID NO 18
<211> LENGTH: 44
<212> TYPE: DNA
<213> ORGANISM: human

<400> SEQUENCE: 18
ctagctgcaa aactggctgc agctgatttc accaggggaa aact                     44

<210> SEQ ID NO 19
<211> LENGTH: 69
<212> TYPE: DNA
<213> ORGANISM: human

<400> SEQUENCE: 19
ctagaagaaa aactggagaa agaagcagct accgctggaa aagcaatgag cgcgctgcac    60
ctgaaaaga                                                            69

<210> SEQ ID NO 20
<211> LENGTH: 51
<212> TYPE: DNA
<213> ORGANISM: human

<400> SEQUENCE: 20
tattatggga ggattctgca ttacctgaag gccaaggagt actcacactg t             51

<210> SEQ ID NO 21
<211> LENGTH: 163
<212> TYPE: DNA
<213> ORGANISM: human
```

```
<400> SEQUENCE: 21
catgagcagt ctgcacctga aaagatatta tggggcaatt gctgcatacc tggcagccaa    60
ggagtactca cactgtcatg agcagtctgc acctgaaaag atattatggg aggattctgc    20
attacctgaa ggccgctgca tactcacact gtgcctggac gat                      63

<210> SEQ ID NO 22
<211> LENGTH: 87
<212> TYPE: DNA
<213> ORGANISM: human

<400> SEQUENCE: 22
catgagcagt ctgcacctga aaagatatta tgggaggatt ctgcattacc tgaaggcaaa    60
ggagtacgct gcatgtgcct ggacgat                                        87

<210> SEQ ID NO 23
<211> LENGTH: 50
<212> TYPE: DNA
<213> ORGANISM: human

<400> SEQUENCE: 23
cgtcagagct gaaatcctag caaactttgc attcattgca agacttacag               50

<210> SEQ ID NO 24
<211> LENGTH: 166
<212> TYPE: PRT
<213> ORGANISM: human

<400> SEQUENCE: 24
```

Met Ser Tyr Asn Leu Leu Gly Phe Leu Gln Arg Ser Ser Asn Phe Gln
 1               5                  10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Ala Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Arg Ile Asn Arg Leu
145                 150                 155                 160

Thr Gly Tyr Leu Arg Asn
                165

```
<210> SEQ ID NO 25
<211> LENGTH: 166
<212> TYPE: PRT
<213> ORGANISM: human
```

```
<400> SEQUENCE: 25

Met Ala Tyr Ala Ala Leu Gly Ala Leu Gln Ala Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Ala
    50                  55                  60

Asn Ile Ala Ser Ile Phe Arg Gln Asp Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Ala Ala Thr
            100                 105                 110

Ala Gly Ala Ala Met Ser Ala Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Arg Ile Asn Arg Leu
145                 150                 155                 160

Thr Gly Tyr Leu Arg Asn
                165

<210> SEQ ID NO 26
<211> LENGTH: 166
<212> TYPE: PRT
<213> ORGANISM: human

<400> SEQUENCE: 26

Met Ser Tyr Asn Leu Leu Gly Phe Leu Gln Arg Ser Ser Asn Ala Ala
1               5                   10                  15

Cys Ala Ala Leu Leu Ala Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Ala Ala Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Ala Leu Met Ser Ser Leu His Leu Lys Arg Tyr Tyr Gly Ala
        115                 120                 125

Ile Ala Ala Tyr Leu Ala Ala Lys Glu Tyr Ser His Cys Ala Trp Thr
    130                 135                 140

Ile Val Arg Val Glu Ile Leu Arg Asn Phe Tyr Arg Ile Asn Arg Leu
145                 150                 155                 160

Thr Gly Tyr Leu Arg Asn
                165
```

```
<210> SEQ ID NO 27
<211> LENGTH: 166
<212> TYPE: PRT
<213> ORGANISM: human

<400> SEQUENCE: 27

Met Ser Tyr Asn Leu Leu Gly Phe Leu Gln Arg Ser Ser Asn Phe Gln
 1               5                  10                  15

Cys Gln Lys Leu Leu Trp Gln Leu Asn Gly Arg Ala Ala Cys Ala
            20                  25                  30

Ala Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Thr Gly Trp Asn
 65                  70                  75                  80

Ala Ser Ile Val Ala Ala Leu Leu Ser Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Ala Leu Met Ser Ser Leu His Leu Lys Arg Tyr Tyr Gly Arg
        115                 120                 125

Ile Leu His Tyr Leu Lys Ala Ala Tyr Ser His Cys Ala Trp Thr
    130                 135                 140

Ile Val Arg Val Glu Ile Leu Arg Asn Phe Tyr Arg Ile Asn Arg Leu
145                 150                 155                 160

Thr Gly Tyr Leu Arg Asn
                165

<210> SEQ ID NO 28
<211> LENGTH: 166
<212> TYPE: PRT
<213> ORGANISM: human

<400> SEQUENCE: 28

Met Ser Tyr Asn Leu Leu Gly Phe Leu Gln Arg Ser Ser Asn Phe Gln
 1               5                  10                  15

Cys Gln Lys Leu Leu Trp Gln Leu Asn Gly Arg Leu Glu Tyr Cys Leu
            20                  25                  30

Lys Asp Arg Ala Ala Phe Ala Ile Pro Ala Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Thr Gly Trp Asn
 65                  70                  75                  80

Glu Thr Ile Val Glu Asn Leu Leu Ala Asn Val Ala His Gln Ile Ala
                85                  90                  95

His Leu Ala Ala Val Leu Glu Glu Lys Leu Glu Lys Glu Asp Phe Thr
            100                 105                 110

Arg Gly Ala Leu Met Ser Ser Leu His Leu Lys Arg Tyr Tyr Gly Arg
        115                 120                 125

Ile Leu His Tyr Leu Lys Ala Lys Glu Tyr Ala Ala Cys Ala Trp Thr
    130                 135                 140
```

-continued

```
Ile Val Arg Val Glu Ile Leu Arg Asn Phe Tyr Arg Ile Asn Arg Leu
145                 150                 155                 160

Thr Gly Tyr Leu Arg Asn
                165

<210> SEQ ID NO 29
<211> LENGTH: 167
<212> TYPE: PRT
<213> ORGANISM: human

<400> SEQUENCE: 29

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Ala Ala Ala Ala
            35                  40                  45

Ala Phe Ala Ala Ala Asp Ala Ala Leu Thr Ile Tyr Glu Met Leu Gln
        50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Ala Tyr His Gln Ala
                85                  90                  95

Asn His Ala Lys Thr Ala Leu Ala Ala Lys Leu Ala Ala Ala Asp Phe
            100                 105                 110

Thr Arg Gly Ala Leu Met Ser Ser Leu His Leu Lys Arg Tyr Tyr Gly
            115                 120                 125

Arg Ile Leu His Tyr Leu Lys Ala Lys Glu Tyr Ser His Cys Ala Trp
        130                 135                 140

Thr Ile Val Arg Ala Glu Ile Leu Ala Asn Phe Ala Arg Ile Ala Arg
145                 150                 155                 160

Leu Thr Gly Tyr Leu Arg Asn
                165
```

POLYMER CONJUGATES OF INTERFERON BETA-1A AND USES

RELATED APPLICATIONS

This is a continuation of PCT/US99/24201, filed on Oct. 15, 1999 as a continuations-in-part of prior U.S. Provisional Ser. No. 60/104,572 filed Oct. 16, 1998 and U.S. Provisional Ser. No. 60/120,161 filed Feb. 16, 1999. The teachings of the earlier-filed patent applications are incorporated herein by reference.

BACKGROUND OF THE INVENTION

Use of polypeptides and proteins for the systemic treatment of specific diseases is now well accepted in medical practice. The role that these substances play in therapy is so important that many research activities are being directed towards the synthesis of large quantities by recombinant DNA technology. Many of these polypeptides are endogenous molecules which are very potent and specific in eliciting their biological actions.

A major factor limiting the usefulness of these proteinaceous substances for their intended application is that, when given parenterally, they are eliminated from the body within a short time. This can occur as a result of metabolism by proteases or by clearance using normal pathways for protein elimination such as by filtration in the kidneys. The oral route of administration of these substances is even more problematic because in addition to proteolysis in the stomach, the high acidity of the stomach destroys them before they reach their intended target tissue. The problems associated with these routes of administration of proteins are well known in the pharmaceutical industry, and various strategies are being used in attempts to solve them.

A great deal of work dealing with protein stabilization has been published. Various ways of conjugating proteins with polymeric materials are known, including use of dextrans, polyvinyl pyrrolidones, glycopeptides, polyethylene glycol and polyamino acids. The resulting conjugated polypeptides are reported to retain their biological activities and solubility in water for parenteral applications.

A peptide family which has been the focus of much clinical work, and efforts to improve its administration and bio-assimilation, is the interferons. Interferons have been tested in a variety of clinical disease states. The use of human interferon beta, one member of that family, is best established in the treatment of multiple sclerosis. Two forms of recombinant interferon beta, have recently been licensed in Europe and the U.S. for treatment of this disease. One form is interferon-beta-1a (trademarked and sold as AVONEX®, mfg. Biogen, Inc., Cambridge, Mass.) and hereinafter, "interferon-beta-1a" or "IFN-beta-1a" or "IFN-β-1a" or "interferon-β-1a", used interchangeably. The other form is interferon-beta-1b (trademarked and sold as BETASERON®. Berlex, Richmond, Calif.), hereinafter, "interferon-beta-1b". Interferon beta-1a is produced in mammalian cells using the natural human gene sequence and is glycosylated, whereas interferon beta-1b is produced in *E. coli* bacteria using a modified human gene sequence that contains a genetically engineered cysteine-to-serine substitution at amino acid position 17 and is non-glycosylated.

Previously, several of us have directly compared the relative in vitro potencies of interferon-beta-1a and interferon beta 1b in functional assays and showed that the specific activity of interferon-beta-1a is approximately 10-fold greater than the specific activity of interferon-beta-1b (Runkel et al., 1998, Pharm. Res. 15: 641–649). From studies designed to identify the structural basis for these activity differences, we identified glycosylation as the only one of the known structural differences between the products that affected the specific activity. The effect of the carbohydrate was largely manifested through its stabilizing role on structure. The stabilizing effect of the carbohydrate was evident in thermal denaturation experiments and SEC analysis. Lack of glycosylation was also correlated with an increase in aggregation and an increased sensitivity to thermal denaturation. Enzymatic removal of the carbohydrate from interferon-beta-1a with PNGase F caused extensive precipitation of the deglycosylated product.

These studies indicate that, despite the conservation in sequence between interferon-beta-1a and interferon-beta-1b, they are distinct biochemical entities and therefore much of what is known about interferon-beta-1b cannot be applied to interferon-beta-1a, and vice versa.

SUMMARY OF THE INVENTION

We have exploited the advantages of glycosylated interferon-beta relative to non-glycosylated forms. In particular, we have developed an interferon-beta-1a composition with increased activity relative to interferon-beta-1b and that also has the salutary properties of pegylated proteins in general with no effective loss in activity as compared to interferon-beta-1a forms that are not conjugated. Thus, if modifications are made in such a way that the products (polymer-interferon-beta 1a conjugates) retain all or most of their biological activities, the following properties may result: altered pharmacokinetics and pharmacodynamics leading to increased half-life and alterations in tissue distribution (e.g, ability to stay in the vasculature for longer periods of time), increased stability in solution, reduced immunogenicity, protection from proteolytic digestion and subsequent abolition of activity. Such a formulation is a substantial advance in the pharmaceutical and medical arts and would make a significant contribution to the management of various diseases in which interferon has some utility, such as multiple sclerosis, fibrosis, and other inflammatory or autoimmune diseases, cancers, hepatitis and other viral diseases. In particular, the ability to remain for longer periods of time in the vasculature allows the interferon beta 1a to be used to inhibit angiogenesis and potentially to cross the blood-brain barrier. Further, the thermal stability gained by creating polymer-interferon-beta-1a conjugates is an advantage when formulating interferon-beta-1a in powder form for use in subsequent administration via inhalation.

We used our knowledge of the crystallographic structure of interferon-beta-1a and developed an interferon-beta-1a-polymer conjugate in which the polymer is linked to those interferon-beta-1a site(s) that will allow the conjugate to retain full activity of the interferon-beta-1a as compared to interferon-beta-1a that is not conjugated.

One aspect of the invention is a conjugated interferon-beta-1a complex wherein the interferon-beta-1a is covalently bonded to a polymer incorporating as an integral part thereof a polyalkylene glycol.

In one particular aspect, the present invention relates to a physiologically active interferon-beta-1a composition comprising physiologically active interferon-beta-1a coupled with a polymer comprising a polyalkylene glycol moiety wherein the interferon-beta-1a and polyalkylene glycol moiety are arranged such that the physiologically active interferon-beta-1a in the composition has an enhanced half life relative to the interferon-beta-1a alone (i.e., in an unconjugated form devoid of the polymer coupled thereto).

Another aspect of the invention is an interferon-beta-1a composition comprising physiologically active interferon-beta-1a coupled with a polymer in which the interferon-beta-1a is a fusion protein, preferably an immunoglobulin fusion. In such a complex, the close proximity of the N-terminus (site of conjugation with polymer) and the C-terminus (site of fusion with the Ig moiety) suggests that polymer conjugation may reduce the immunogenicity of the fusion protein.

In another aspect, the present invention relates to a physiologically active interferon-beta-1a composition comprising physiologically active interferon-beta-1a coupled with a polymer comprising a polyalkylene glycol moiety wherein the interferon-beta-1a and polyalkylene glycol moiety are arranged such that the physiologically active interferon-beta-1a in the composition has an enhanced activity relative to interferon-beta-1b alone (i.e., in an unconjugated form devoid of the polymer coupled thereto).

Another embodiment of the invention is a conjugated interferon-beta-1a protein whose interferon-beta-1a moiety has been mutated to provide for muteins with selectively enhanced antiviral and/or antiproliferative activity relative to non-mutated forms of interferon-beta-1a.

The invention relates to a further aspect to a stable, aqueously soluble, conjugated interferon-beta-1a complex comprising a physiologically active interferon-beta-1a covalently coupled to a physiologically compatible polyethylene glycol moiety. In such complex, the interferon-beta-1a may be covalently coupled to the physiologically compatible polyethylene glycol moiety by a labile covalent bond at a free amino acid group of the interferon-beta-1a, wherein the labile covalent bond is severed in vivo by biochemical hydrolysis and/or proteolysis.

In another aspect, the present invention relates to a dosage form comprising a pharmaceutically acceptable carrier and a stable, aqueously soluble, interferon-beta 1a complex comprising interferon-beta coupled to a physiologically compatible polyethylene glycol.

In another aspect, covalently coupled interferon-beta-1a compositions such as those described above may utilize interferon-beta-1a intended for diagnostic or in vitro applications, wherein the interferon-beta-1a is for example a diagnostic reagent for immunoassay or other diagnostic or non-in vivo applications. In such non-therapeutic applications, the complexes of the invention are highly usefully employed as stabilized compositions which may for example be formulated in compatible solvents or other solution-based formulations to provide stable compositional forms which are of enhanced resistance to degradation.

Modification of interferon-beta 1a with a non-toxic polymer may offer certain advantages. If modifications are made in such a way that the products (polymer-interferon-beta 1a conjugates) retain all or most of their biological activities the following properties may result: altered pharmacokinetics and pharmacodynamics leading to increased half-life and alterations in tissue distribution (e.g, ability to stay in the vasculature for longer periods of time), increased stability in solution, reduced immunogenicity, protection of the modified interferon-beta 1a from proteolytic digestion and subsequent abolition of activity; increased thermal stability leading to more effective formulation of powdered interferon-beta-1a for oral or inhaled use.

Interferon-beta-1a endowed with the improved properties described above may be effective as therapy following either oral, aerosol, or parenteral administration. Other routes of administration, such as nasal and transdermal, may also be possible using the modified interferon-beta 1a.

Another aspect of the invention is a method of inhibiting angiogenesis and neovascularization comprising subject an effective amount of the compositions of the invention. As a result of increasing the level and duration of the interferon in the vasculature, the pegylated product of the invention should be particularly effective as an angiogenesis inhibitor.

In non-therapeutic (e.g., diagnostic) applications, conjugation of diagnostic and/or reagent species of interferon-beta is also contemplated. The resulting conjugated agent is resistant to environmental degradative factors, including solvent- or solution-mediated degradation processes. As a result of such enhanced resistance and increased stability of interferon-beta-1a, the stability of the active ingredient is able to be significantly increased, with concomitant reliability of the interferon-beta-1a containing composition in the specific end use for which same is employed.

Other aspects, features, and modifications of the invention will be more fully apparent from the ensuing disclosure and appended claims.

The binding affinities of the alanine substituted IFN mutants (A1–E) for the IFNAR2 receptor chain were determined as described in Example 1 (subsection D). The histogram presents their binding affinities in this assay relative to wild type his-IFN-beta (% w.t.). The % w.t. values were calculated as the (affinity of wild type his-IFN-beta)/affinity of mutant IFN-beta×100. The % w.t. (O) for individual experiments (n=3) and an average % w.t. (x) for the experimental set are shown. Mutants A2, AB1, AB2, and E did not bind IFNAR2/Fc at concentrations 500-fold higher than the w.t. his-IFN-beta EC 50 (*)

Figure 2:
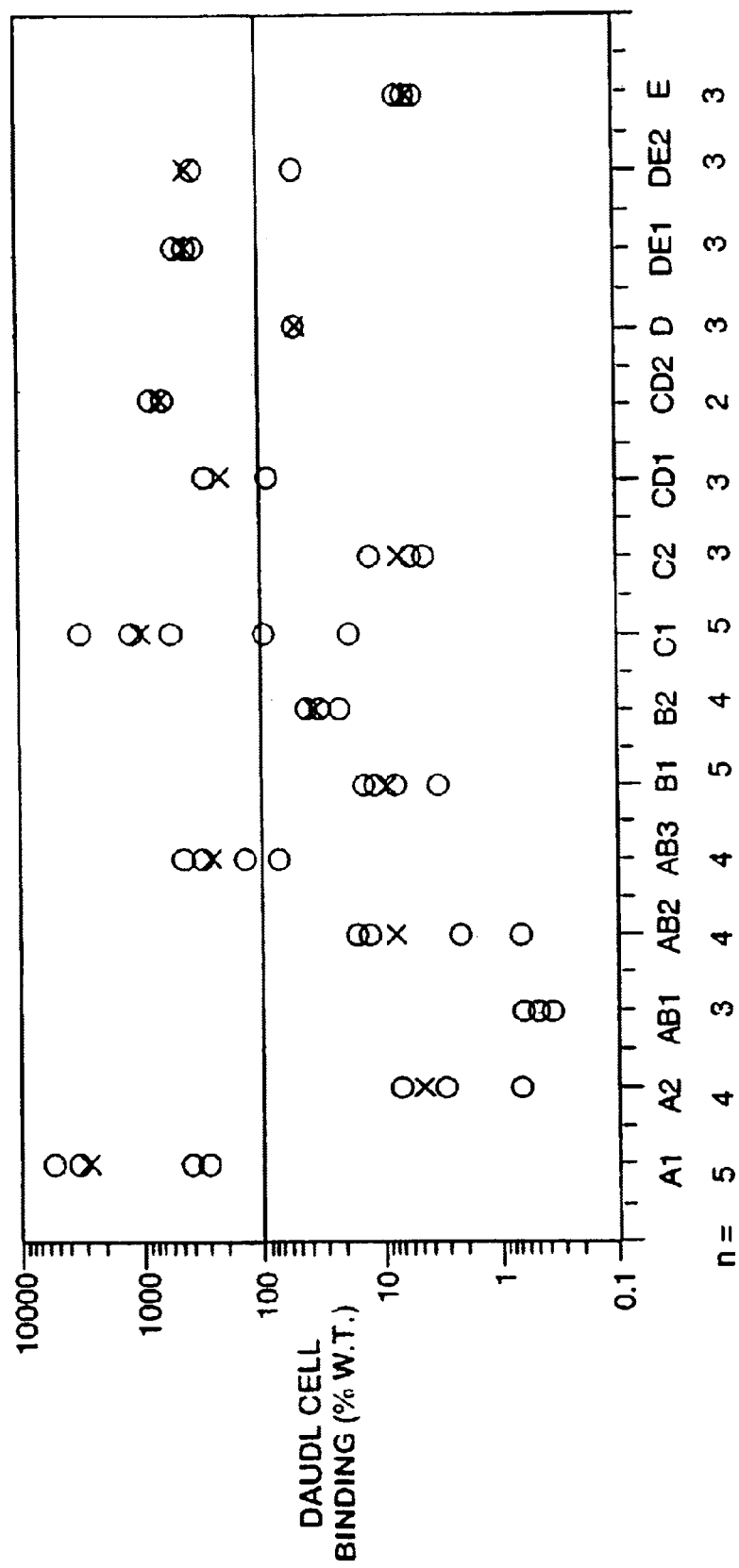

FIG. 2. Binding of alanine substituted interferon-beta-1a mutants to the type I interferon cell surface receptor complexes ("IFNAR½ complex") expressed on Daudi Burkitt's lymphoma cells. The receptor binding properties of the alanine substitution mutants (A1–E) were determined using a FACS based, cell surface receptor binding assay as described in Example 1(subsection D). The histogram presents their receptor binding affinities in this assay relative to wild type his-IFN-beta (% w.t.). The % w.t. for each mutant was calculated as the (affinity of wild type his-IFN-beta)/affinity of mutant IFN-beta×100. The % w.t. values (O) for individual experiments and an average of the % w.t. values for the experimental set (x) are shown.

Figure 3:
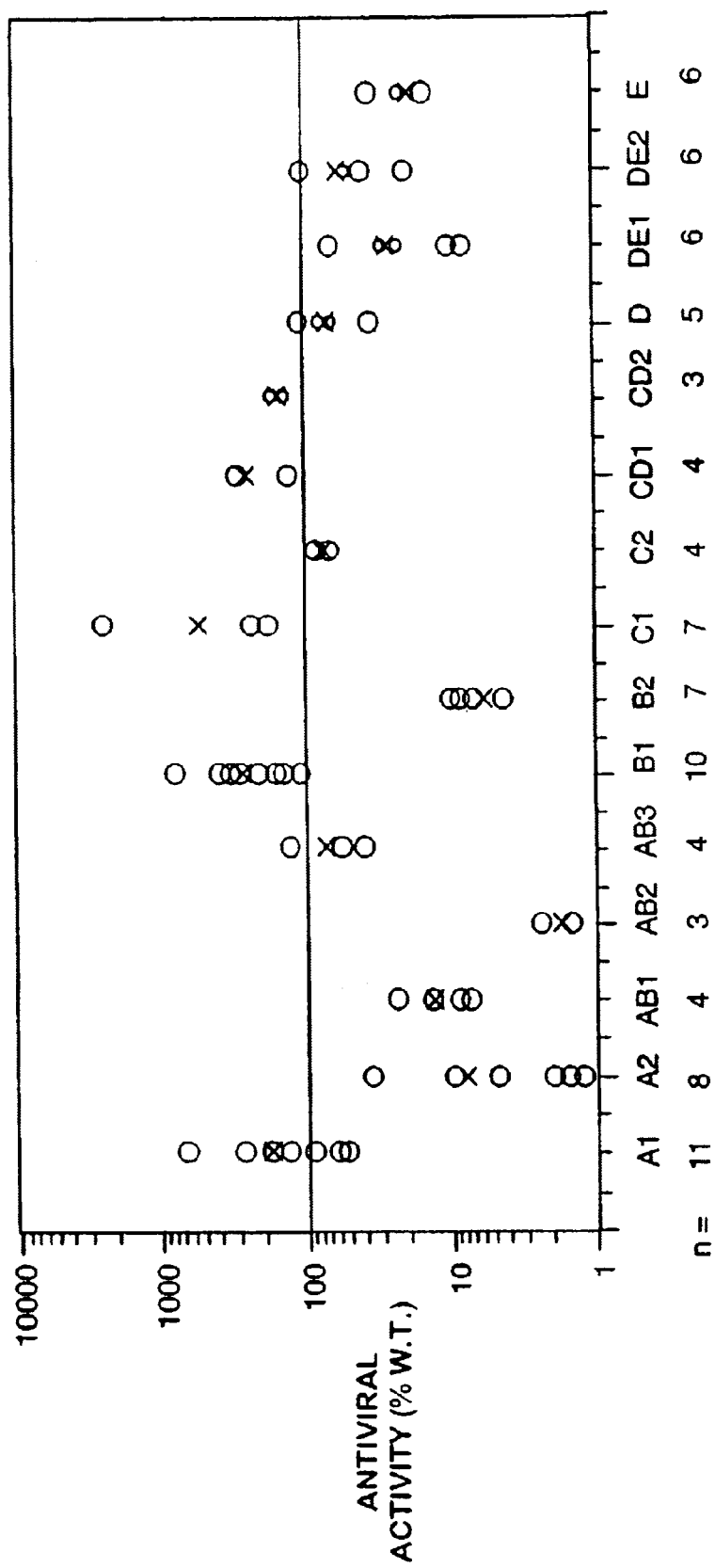

FIG. 3. Antiviral activities of alanine substituted interferon-beta-1a mutants

The antiviral activities of the alanine substitution mutants (A1–E) were determined on human A549 cells challenged with EMC virus as described in Example 1 (subsection E). The histogram presents their activities in this assay relative to wild type his-IFN-beta (% w.t.). The % w.t. was calculated as the (concentration of w.t. his-IFN-beta [50% cpe]/concentration of mutant IFN-beta [50% cpe]×100. The % w.t ( ) for multiple assays and the average of the experimental data set (x) are shown.

Figure 4:
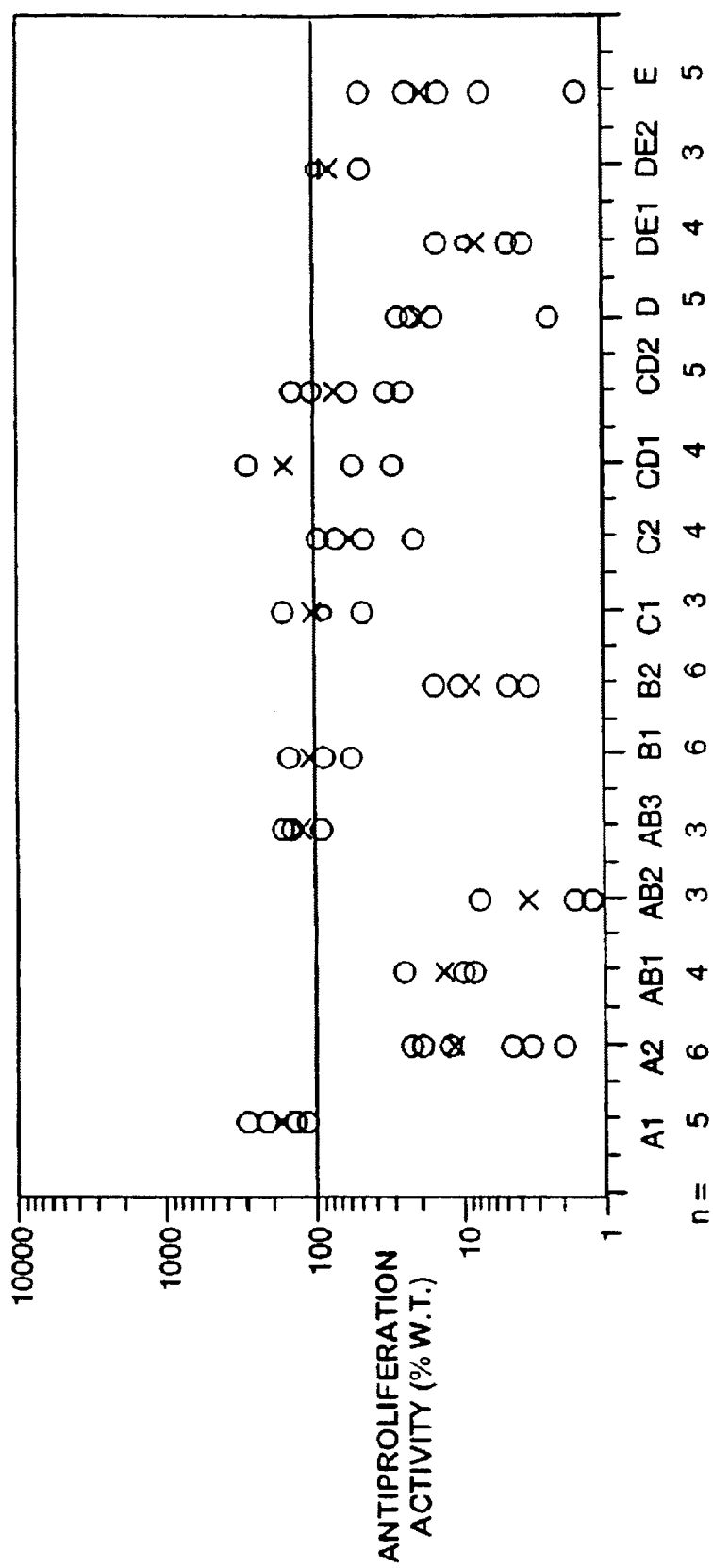
Figure 5:
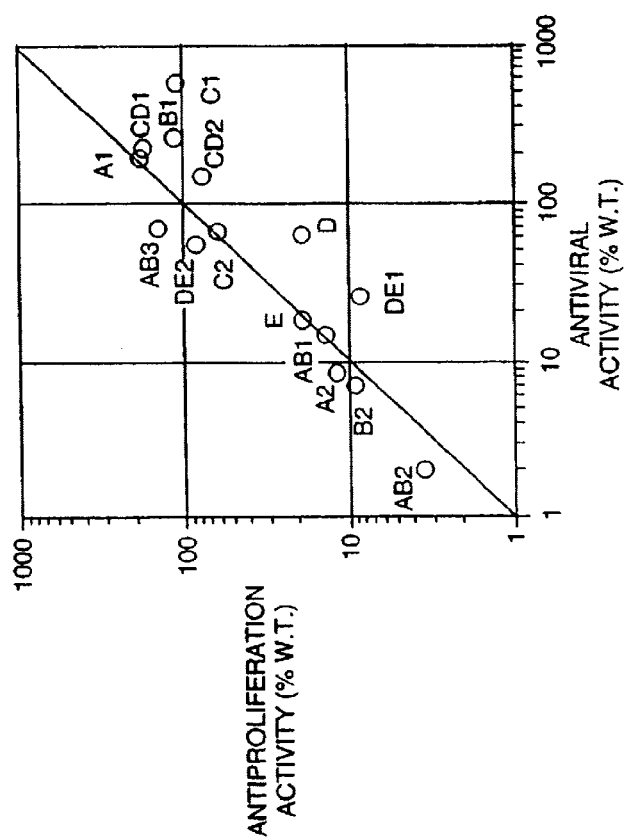

FIG. 4. Antiproliferative activities of alanine substituted interferon-beta-1a mutants The antiproliferation activity of the alanine substitution mutants (A1–E) were determined on Daudi Birkitt's lymphoma cells as described in Example 1 (subsection E). The histogram presents their activities in this assay relative to wild type his-IFN-beta (% w.t). The % w.t. was calculated as (concentration w.t his-IFN-beta [50% growth inhibition]/concentration of mutant IFN-beta [50% growth inhibition]×100. The % w.t (0) for multiple assays and the average of the experimental data set (x) are shown FIG. 5. Relative antiviral and antiproliferative activities of alanine substituted interferon-beta-1a mutants. The relative activities of alanine substitution mutants (A1–E) in the antiviral (x axis) and antiproliferation (y axis) assays were compared. The average percent wild type his-IFN-beta (% w.t., x) presented in FIGS. 3 and 4 were used for this comparison. Those mutants that display a coordinate change in both activities would fall on the vertical line. Those mutants that display a change in antiviral activity that is disproportionate to the change in antiproliferation activity fall significantly off the diagonal line (DE1, D, C1). Significance was determined from consideration of standard deviations inherent in the average % w.t. values used.

Figure 6:
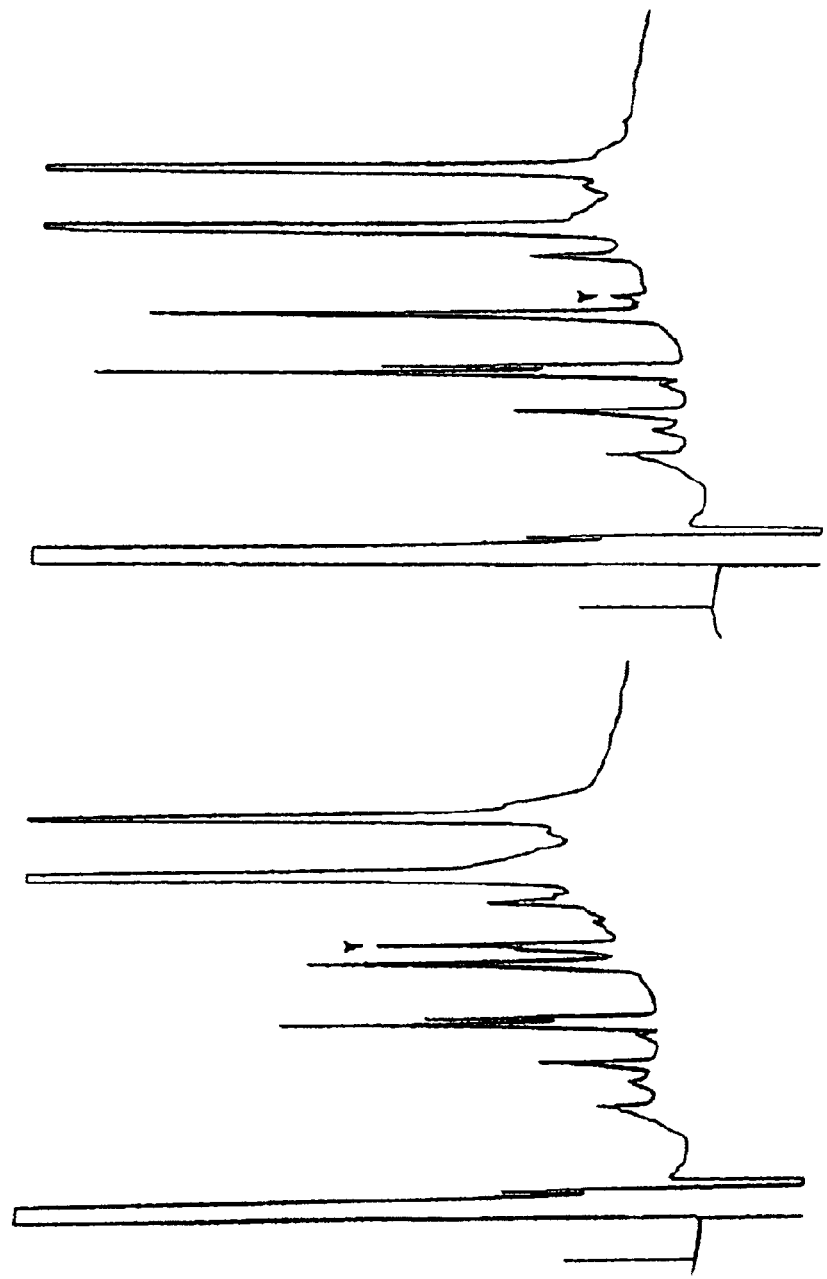

FIG. 6. Localization of the site of pegylation by peptide mapping. Pegylated and unmodified interferon-β-1a were subjected to peptide mapping analysis. Samples were digested with endoproteinase Lys-C and subjected to reverse phase HPLC on a $C_4$ column. The column was developed with a 0–70% gradient of acetonitrile in 0.1% trifluoroacetic acid. The column effluent was monitored at 214 nm. Panel a, unmodified interferon-β-1a. Panel b, pegylated interferon-β-1a. Arrowheads mark the elution position of the N-terminal endoproteinase Lys peptide of interferon-β-1a containing amino acid resides 1–19.

Figure 7:
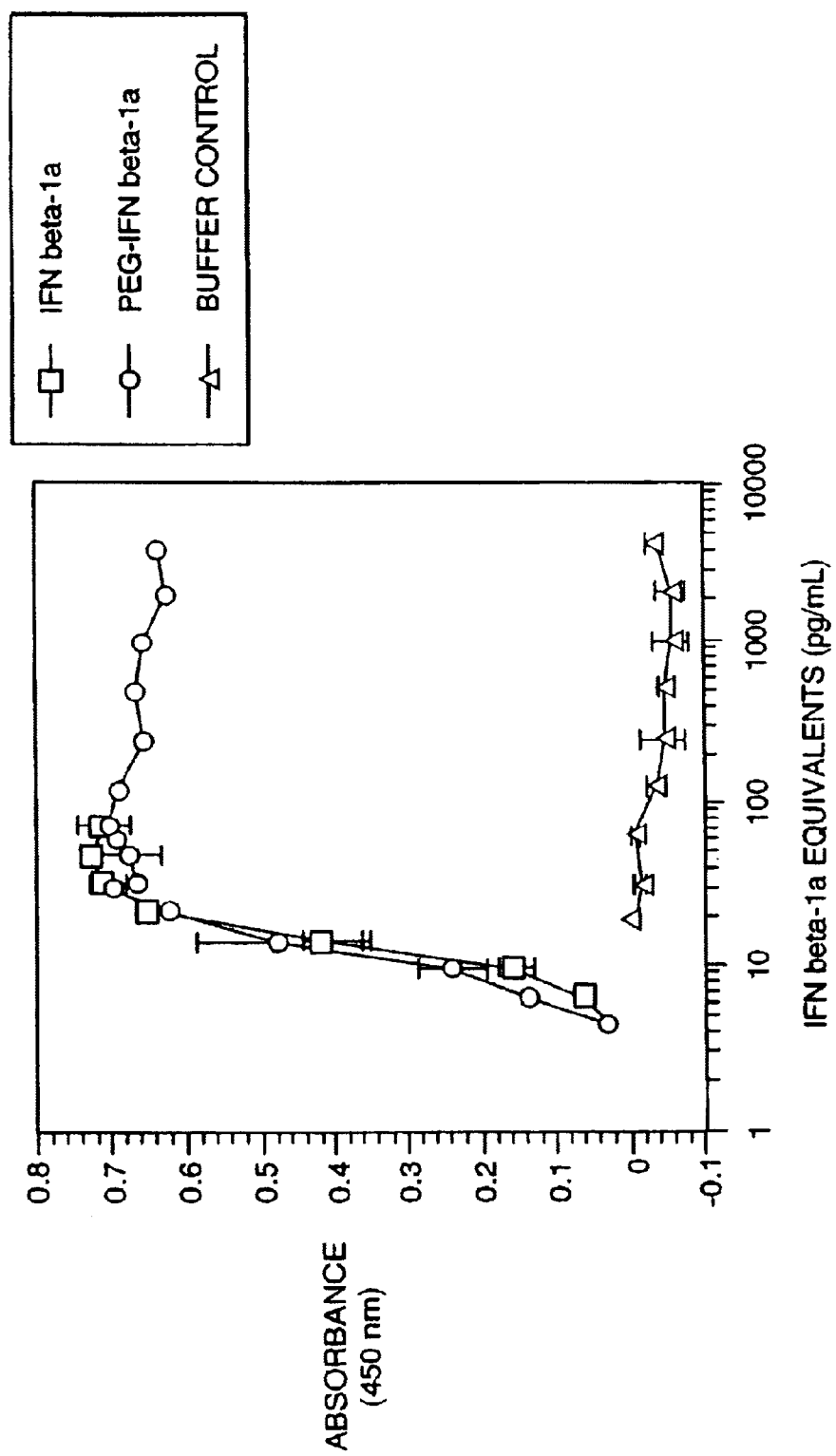

FIG. 7. Antiviral Activity of Conjugated and Non-Conjugaged Interferon-beta-1a.

The activity of interferon-beta-1a or PEGylated interferon-beta-1a at the concentrations indicated on the X axis were assessed in antiviral assays using human lung carcinoma (A549) cells challenged with encephalomyocarditis virus. Following a two day incubation with virus, viable cells were stained with MTT, the plates were read at 450 nm, and the absorbance which is reflective of cell viability is shown on the Y axis. The standard deviations are shown as error bars. The concentration of interferon-beta-1a or PEGylated interferon beta-1a which offered 50% viral killing (the "50% cytopathic effect") (50% maximum OD450) was about 11 pg/ml and the 50% cytopathic effect for PEGylated interferon-beta-1a was about 11 pg/ml.

Figure 8A:
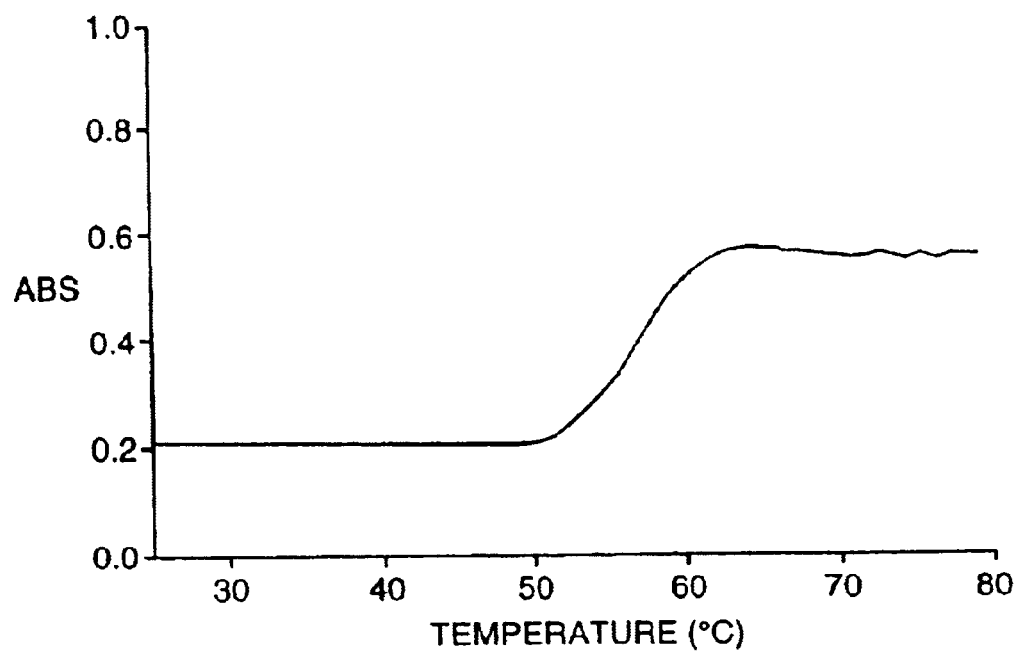
Figure 8B:
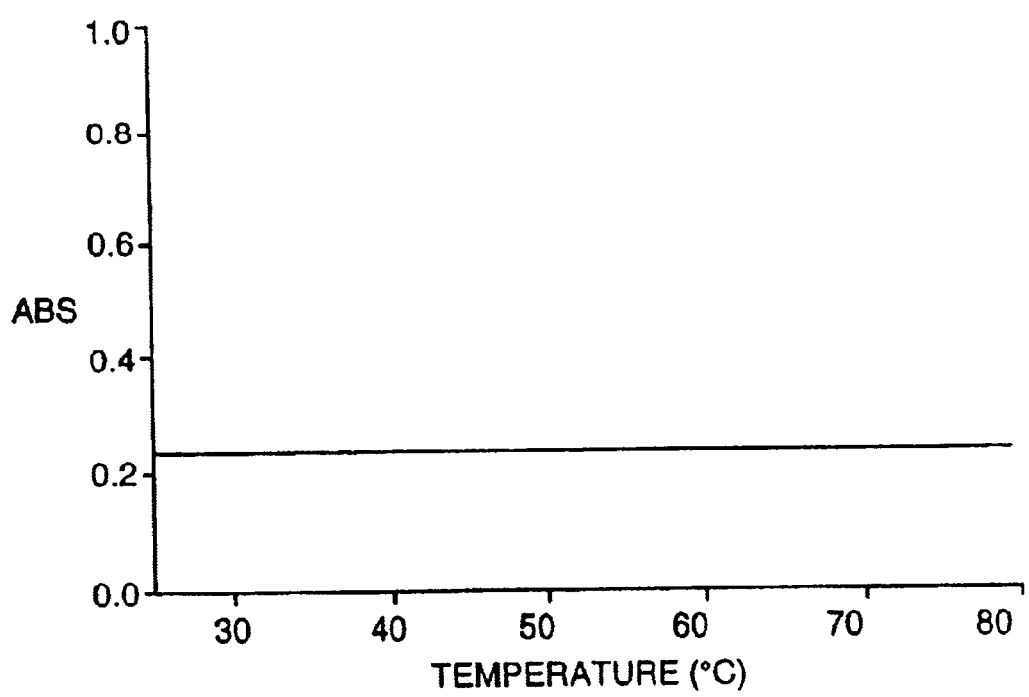

FIG. 8. Assessing stabilization of conjugates using thermal denaturation

PEGylated interferon-beta-1a and untreated interferon-beta-1a control in 20 mM HEPES pH 7.5, 20 mM NaCl were heated at a fixed rates of 1 degree/min. Denaturation was followed by monitoring absorbance changes at 280 nm. (a) unmodified interferon-beta-1a (b) PEGylated interferon-beta-1a.

Figure 9:
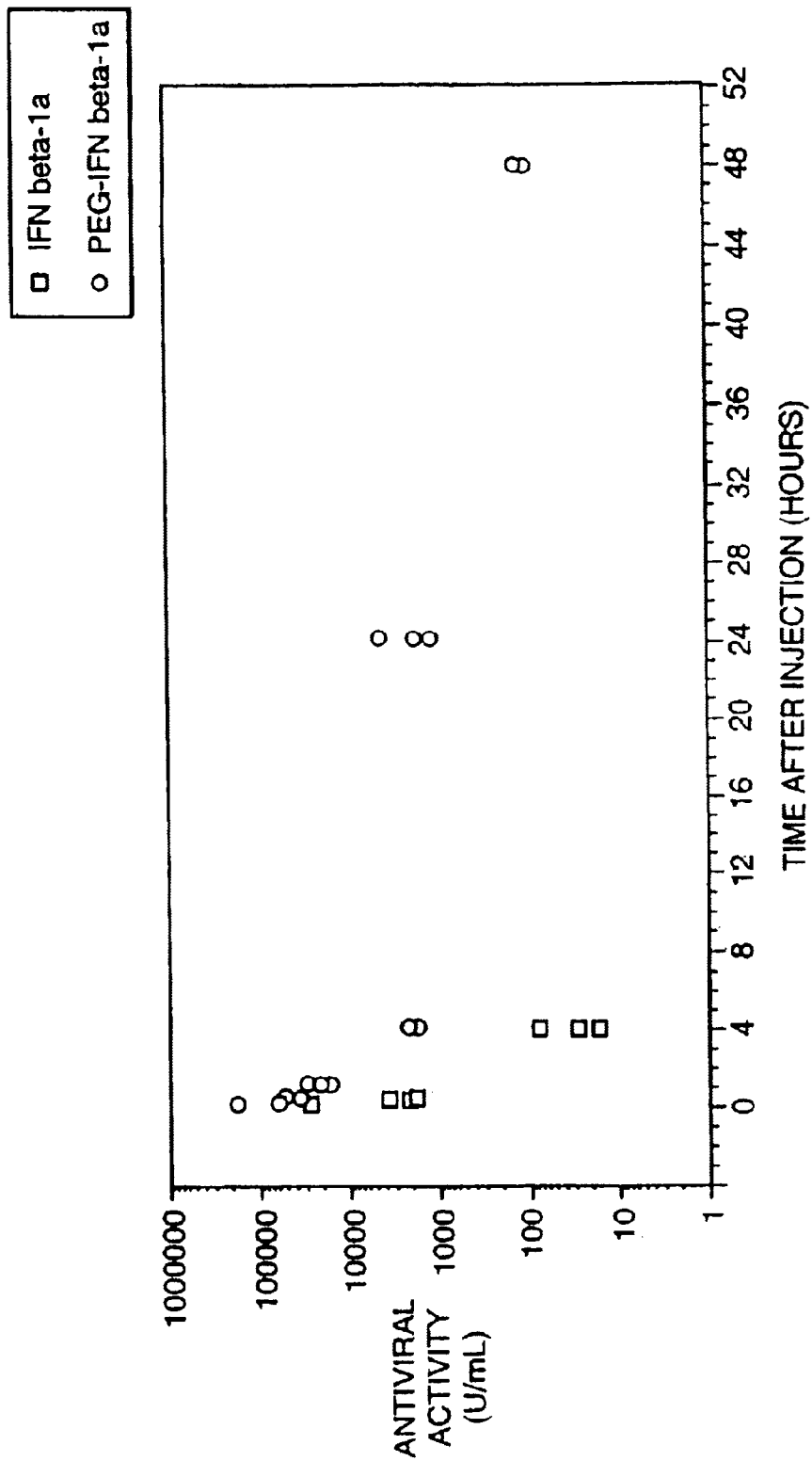

FIG. 9. Measurements of interferon-beta antiviral activity in the plasma of mice treated with interferon-beta-1a or PEGylated interferon-beta-1a.

Mice are injected iv with either 50,000 Units of interferon-beta-1a or 50,000 Units of pegylated-interferon-beta-1a (containing the 20K PEG). Blood from these mice is obtained via retro-orbital bleeds at various times after interferon injection as indicated on the X axis. There are at least 3 mice bled at each time point, and plasma is prepared and frozen until the time interferon-beta activity is evaluated in antiviral assays using human lung carcinoma (A549) cells challenged with encephalomyocarditis virus. Viable cells were stained with a solution of MTT, the plates were read at 450 nm, to determine the absorbance which is reflective of cell viability and interferon-beta activity. Standard curves were generated for each plate using interferon-beta-1a and used to determine the amount of interferon-beta activity in each sample. Data from the individual animals are shown.

FIG. 10. Full DNA sequence of histidine-tagged interferon beta gene and its protein product. The full DNA (SEQ ID NO: 1) and protein (SEQ ID NO: 2) sequences of the histidine-tagged IFN-beta-1a are shown. The cleaved VCAM-1 signal sequence leaves 3 amino terminal residues (SerGlyGly) upstream of the histidine tag ($His_6$, positions 4–9). The enterokinase linker sequence (AspAspAspAspLys) is separate from the histidine tag by a spacer (positions 10–12, SerSerGly). The natural IFN-beta-1a protein sequence spans positions (Met18–Asn183).

Figure 11:
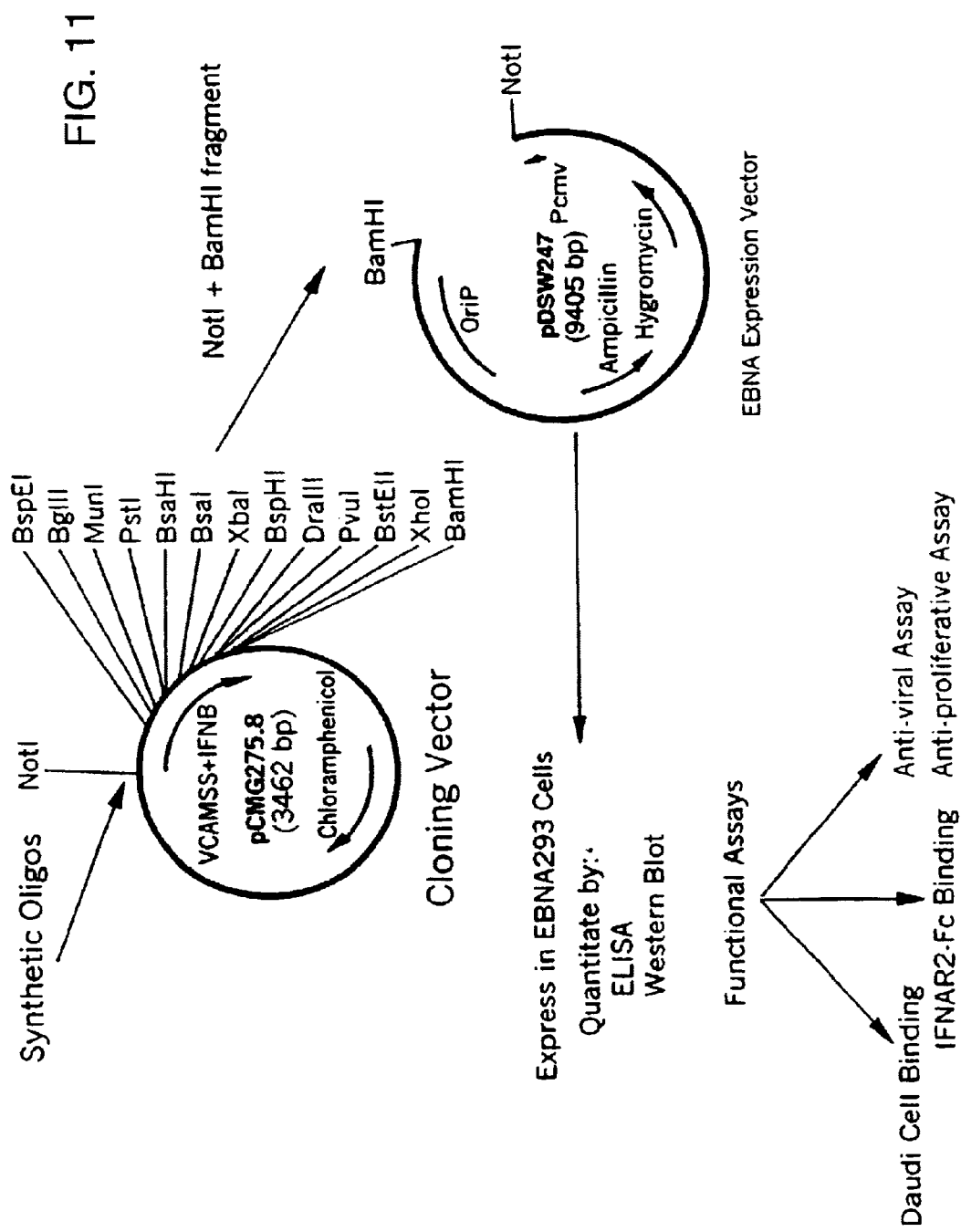

FIG. 11. Schematic representation of overall cloning and expression strategy.

DETAILED DESCRIPTION OF THE INVENTION

Definitions

As used herein, the term "covalently coupled" means that the specified moieties are either directly covalently bonded to one another, or else are indirectly covalently joined to one another through an intervening moiety or moieties, such as a bridge, spacer, or linkage moiety or moieties.

Interferon—An "interferon" (also referred to as "IFN") is a small, species-specific, single chain polypeptide, produced by mammalian cells in response to exposure to a variety of inducers such as viruses, polypeptides, mitogens and the like. The most preferred interferon used in the invention is glycosylated, human, interferon-beta that is glycosylated at residue 80 (Asn 80) and that is preferably derived via recombinant DNA technologies. This preferred glycosylated interferon-beta is called "interferon-beta-1a" or "IFN-beta-1a" or "IFN-ᗡ-1a" or "interferon beta 1a" or "interferon-ᗡ-1a", all used interchangeably. The term "interferon-beta-1a" is also meant to encompass mutants thereof (e.g., Example 1), provided that such mutants are also glycosylated at residue 80 (Asn 80). Recombinant DNA methods for producing proteins, including interferons are known. See for example, U.S. Pat. Nos. 4,399,216, 5,149,636, 5,179,017 (Axel et al) and U.S. Pat. No. 4,470,461 (Kaufman).

Preferred interferon-beta-1a polynucleotides that may be used in the present methods of the invention are derived from the wild-type interferon beta gene sequences of various vertebrates, preferably mammals and are obtained using methods that are well-known to those having ordinary skill in the art such as the methods described in the following U.S. Patents: U.S. Pat. No. 5,641,656 (issued Jun. 24, 1997: DNA encoding avian type I interferon proprotein and mature avian type I interferon), U.S. Pat. No. 5,605,688 (Feb. 25, 1997—recombinant dog and horse type I interferons); U.S. Pat. No. 5,231,176 (Jul. 27, 1993, DNA molecule encoding a human leukocyte interferon); U.S. Pat. No. 5,071,761 (Dec. 10, 1991, DNA sequence coding for sub-sequences of human lymphoblastoid interferons LyIFN-alpha-2 and LyIFN-alpha-3); U.S. Pat. No. 4,970,161 (Nov. 13, 1990, DNA sequence coding for human interferon-gamma); U.S. Pat. No. 4,738,931 (Apr. 19, 1988, DNA containing a human interferon beta gene); U.S. Pat. No. 4,695,543 (Sep. 22, 1987, human alpha-interferon Gx-1 gene and U.S. Pat. No. 4,456,748 (Jun. 26, 1984, DNA encoding sub-sequences of different, naturally, occurring leukocyte interferons).

Mutants of interferon-beta-1a may be used in accordance with this invention. Mutations are developed using conventional methods of directed mutagenesis, known to those of ordinary skill in the art. Moreover, the invention provides for functionally equivalent interferon-beta-1a polynucleotides that encode for functionally equivalent interferon-beta-1a polypeptides.

A first polynucleotide encoding interferon-beta-1a is "functionally equivalent" compared with a second polynucleotide encoding interferon-beta-1a if it satisfies at least one of the following conditions:

(a): the "functional equivalent" is a first polynucleotide that hybridizes to the second polynucleotide under standard hybridization conditions and/or is degenerate to the first polynucleotide sequence. Most preferably, it encodes a mutant interferon having the activity of an interferon-beta-1a;

(b) the "functional equivalent" is a first polynucleotide that codes on expression for an amino acid sequence encoded by the second polynucleotide.

In summary, the term "interferon" includes, but is not limited to, the agents listed above as well as their functional equivalents. As used herein, the term "functional equivalent" therefore refers to an interferon-beta-1a protein or a polynucleotide encoding the interferon-beta-1a protein that has the same or an improved beneficial effect on the mammalian recipient as the interferon of which it is deemed a functional equivalent. As will be appreciated by one of ordinary skill in the art, a functionally equivalent protein can be produced by recombinant techniques, e.g., by expressing a "functionally equivalent DNA". Accordingly, the instant invention embraces interferon-beta-1a proteins encoded by naturally-occurring DNAs, as well as by non-naturally-occurring DNAs which encode the same protein as encoded by the naturally-occurring DNA. Due to the degeneracy of the nucleotide coding sequences, other polynucleotides may be used to encode interferon-beta-1a. These include all, or portions of the above sequences which are altered by the substitution of different codons that encode the same amino acid residue within the sequence, thus producing a silent change. Such altered sequences are regarded as equivalents of these sequences. For example, Phe (F) is coded for by two codons, TTC or TTT, Tyr (Y) is coded for by TAC or TAT and His (H) is coded for by CAC or CAT. On the other hand, Trp (W) is coded for by a single codon, TGG. Accordingly, it will be appreciated that for a given DNA sequence encoding a particular interferon there will be many DNA degenerate sequences that will code for it. These degenerate DNA sequences are considered within the scope of this invention.

"fusion"—refers to a co-linear linkage of two or more proteins or fragments thereof via their individual peptide backbones through genetic expression of a polynucleotide molecule encoding those proteins. It is preferred that the proteins or fragments thereof be from different sources. Thus, preferred fusion proteins include an interferon-beta-1a protein or fragment covalently linked to a second moiety that is not an interferon. Specifically, an "interferon-beta-1a/Ig fusion" is a protein comprising an interferon-beta-1a molecule of the invention, or fragment thereof linked to an N-terminus of an immunoglobulin chain wherein a portion of the N-terminus of the immunoglobulin is replaced with the interferon-beta-1a.

"Recombinant," as used herein, means that a protein is derived from recombinant, mammalian expression systems. Protein expressed in most bacterial cultures, e.g., E. coli, will be free of glycan so these expression systems are not preferred. Protein expressed in yeast may have a oligosaccharide structures that are different from that expressed in mammalian cells.

"Biologically active," as used throughout the specification as a characteristic of interferon-beta 1a, means that a particular molecule shares sufficient amino acid sequence homology with the embodiments of the present invention disclosed herein to be capable of antiviral activity as measured in an in vitro antiviral assay of the type shown in Example 1 (see below).

A "therapeutic composition" as used herein is defined as comprising the proteins of the invention and other physiologically compatible ingredients. The therapeutic composition may contain excipients such as water, minerals and carriers such as protein.

An "effective amount" of an agent of the invention is that amount which produces a result or exerts an influence on the particular condition being treated.

"amino acid"—a monomeric unit of a peptide, polypeptide, or protein. There are twenty amino acids found in naturally occurring peptides, polypeptides and proteins, all of which are L-isomers. The term also includes analogs of the amino acids and D-isomers of the protein amino acids and their analogs.

A "derivatized" amino acid is a natural or nonnatural amino acid in which the normally occurring side chain or end group is modified by chemical reaction. Such modifications include, for example, gamma-carboxylation, beta-carboxylation, sulfation, sulfonation, phosphorylation, amidization, esterification, N-acetylation, carbobenzylation, tosylation, and other modifications known in the art. A "derivatized polypeptide" is a polypeptide containing one or more derivatized amino acids.

"protein"—any polymer consisting essentially of any of the 20 amino acids. Although "polypeptide" is often used in reference to relatively large polypeptides, and "peptide" is often used in reference to small polypeptides, usage of these terms in the art overlaps and is varied. The term "protein" as used herein refers to peptides, proteins and polypeptides, unless otherwise noted.

"mutant"—any change in the genetic material of an organism, in particular any change (i.e., deletion, substitution, addition, or alteration) in a wild-type polynucleotide sequence or any change in a wild-type protein. The term "mutein" is used interchangeably with "mutant".

"wild-type"—the naturally-occurring polynucleotide sequence of an exon of a protein, or a portion thereof, or protein sequence, or portion thereof, respectively, as it normally exists in vivo.

"standard hybridization conditions"—salt and temperature conditions substantially equivalent to 0.5×SSC to about 5×SSC and 65° C. for both hybridization and wash. The term "standard hybridization conditions" as used herein is therefore an operational definition and encompasses a range of hybridization conditions. Higher stringency conditions may, for example, include hybridizing with plaque screen buffer (0.2% polyvinylpyrrolidone, 0.2% Ficoll 400; 0.2% bovine serum albumin, 50 mM Tris-HCl (pH 7.5); 1 M NaCl; 0.1% sodium pyrophosphate; 1% SDS); 10% dextran sulfate, and 100 µg/ml denatured, sonicated salmon sperm DNA at 65° C. for 12–20 hours, and washing with 75 mM NaCl/7.5 mM sodium citrate (0.5×SSC)/1% SDS at 65° C. Lower stringency conditions may, for example, include hybridizing with plaque screen buffer, 10% dextran sulfate and 110 µg/ml denatured, sonicated salmon sperm DNA at 55° C. for 12–20 hours, and washing with 300 mM NaCl/30 mM sodium citrate (2.0×SSC)/1% SDS at 55° C. See also Current Protocols in Molecular Biology, John Wiley & Sons, Inc. New York, Sections 6.3.1–6.3.6, (1989).

"expression control sequence"—a sequence of polynucleotides that controls and regulates expression of genes when operatively linked to those genes.

"operatively linked"—a polynucleotide sequence (DNA, RNA) is operatively linked to an expression control sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the polynucleotide sequence under the control of the expression control sequence and production of the desired polypeptide encoded by the polynucleotide sequence.

"expression vector"—a polynucleotide, such as a DNA plasmid or phage (among other common examples) which allows expression of at least one gene when the expression vector is introduced into a host cell. The vector may, or may not, be able to replicate in a cell.

"Isolated" (used interchangeably with "substantially pure")—when applied to nucleic acid i.e., polynucleotide sequences, that encode polypeptides, means an RNA or DNA polynucleotide, portion of genomic polynucleotide, cDNA or synthetic polynucleotide which, by virtue of its origin or manipulation: (i) is not associated with all of a polynucleotide with which it is associated in nature (e.g., is present in a host cell as an expression vector, or a portion thereof); or (ii) is linked to a nucleic acid or other chemical moiety other than that to which it is linked in nature; or (iii) does not occur in nature. By "isolated" it is further meant a polynucleotide sequence that is: (i) amplified in vitro by, for example, polymerase chain reaction (PCR); (ii) chemically synthesized; (iii) recombinantly produced by cloning; or (iv) purified, as by cleavage and gel separation.

Thus, "substantially pure nucleic acid" is a nucleic acid which is not immediately contiguous with one or both of the coding sequences with which it is normally contiguous in the naturally occurring genome of the organism from which the nucleic acid is derived. Substantially pure DNA also includes a recombinant DNA which is part of a hybrid gene encoding additional sequences.

"Isolated" (used interchangeably with "substantially pure")—when applied to polypeptides means a polypeptide or a portion thereof which, by virtue of its origin or manipulation: (i) is present in a host cell as the expression product of a portion of an expression vector; or (ii) is linked to a protein or other chemical moiety other than that to which it is linked in nature; or (iii) does not occur in nature. By "isolated" it is further meant a protein that is: (i) chemically synthesized; or (ii) expressed in a host cell and purified away from associated proteins. The term generally means a polypeptide that has been separated from other proteins and nucleic acids with which it naturally occurs. Preferably, the polypeptide is also separated from substances such as antibodies or gel matrices (polyacrylamide) which are used to purify it.

"heterologous promoter"—as used herein is a promoter which is not naturally associated with a gene or a purified nucleic acid.

"Homologous"—as used herein is synonymous with the term "identity" and refers to the sequence similarity between two polypeptides, molecules or between two nucleic acids. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are homologous at that position. The percentage homology between two sequences is a function of the number of matching or homologous positions shared by the two sequences divided by the number of positions compared×100. For instance, if 6 of 10 of the positions in two sequences are matched or are homologous, then the two sequences are 60% homologous. By way of example, the DNA sequences CTGACT and CAGGTT share 50% homology (3 of the 6 total positions are matched). Generally, a comparison is made when two sequences are aligned to give maximum homology. Such alignment can be provided using, for instance, the method of Needleman et al., *J. Mol Biol.* 48: 443–453 (1970), implemented conveniently by computer programs such as the Align program (DNAstar, Inc.). Homologous sequences share identical or similar amino acid residues, where similar residues are conservative substitutions for, or "allowed point mutations" of, corresponding amino acid residues in an aligned reference sequence. In this regard, a "conservative substitution" of a residue in a reference sequence are those substitutions that are physically or functionally similar to the corresponding reference residues, e.g., that have a similar size, shape, electric charge, chemical properties, including the ability to form covalent or hydrogen bonds, or the like. Particularly preferred conservative substitutions are those fulfilling the criteria defined for an "accepted point mutation" in Dayhoff et al., 5: Atlas of Protein Sequence and Structure, 5: Suppl. 3, chapter 22: 354–352, Nat. Biomed. Res. Foundation, Washington, D.C. (1978).

The terms polynucleotide sequence" and "nucleotide sequence" are also used interchangeably herein.

"angiogenesis" and "neovascularization" means, in their broadest sense, the recruitment of new blood vessels. In particular, angiogenesis also refers to the recruitment of new blood vessels at a tumor site.

"IFNAR2", "IFNAR1", "IFNAR½" refer to the proteins knows to compose the cell surface type I interferon receptor. The extracellular portion (ectodomain) portion of the IFNAR2 chain alone can bind interferon alpha or beta.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, Molecular Cloning: A Laboratory Manual, 2nd edition. (Sambrook, Fritsch and Maniatis, eds.), Cold Spring Harbor Laboratory Press, 1989; DNA Cloning, Volumes I and II (D. N. Glover, ed), 1985; Oligonucleotide Synthesis, (M. J. Gait, ed.), 1984; U.S. Pat. No. 4,683,195 (Mullis et al.,); Nucleic Acid Hybridization (B. D. Hames and S. J. Higgins, eds.), 1984; Transcription and Translation (B. D. Hames and S. J. Higgins, eds.), 1984; Culture of Animal Cells (R. I. Freshney, ed). Alan R. Liss, Inc., 1987; Immobilized Cells and Enzymes, IRL Press, 1986; A Practical Guide to Molecular Cloning (B. Perbal), 1984; Methods in Enzymology, Volumes 154 and 155 (Wu et al., eds), Academic Press, New York; Gene Transfer Vectors for Mammalian Cells (J. H. Miller and M. P. Calos, eds.), 1987, Cold Spring Harbor Laboratory; Immunochemical Methods in Cell and Molecular Biology (Mayer and Walker, eds.), Academic Press, London, 1987; Handbook of Experiment Immunology, Volumes I–IV (D. M. Weir and C. C. Blackwell, eds.), 1986; Manipulating the Mouse Embryo, Cold Spring Harbor Laboratory Press, 1986.

The Interferon-beta

Interferon-beta-1a is useful as an agent for the treatment, remission or attenuation of a disease state, physiological condition, symptoms, or etiological factors, or for the evaluation or diagnosis thereof. The term also refers to interferon-beta-1a that is itself part of a fusion protein such as an immunoglobulin-interferon-beta-1a fusion protein, as described in co-pending applications Ser. Nos. 60/104,572 and 60/120,161. Preparation of fusion proteins generally are well within the knowledge of persons having ordinary skill in the art.

We found unique site(s) for polymer attachment that would not destroy function of the interferon-beta-1a. In addition, we also used site-directed mutagenesis methods to independently investigate site(s) for polymer attachment (See Example 1). Briefly, we undertook a mutational analysis of human interferon-beta-1a with the aim of mapping resides required for activity and receptor binding. The availability of the 3-D crystal structure of human interferon-beta-1a (see above and Example 1) allows us to identify, for alanine (or serine) substitutions, the solvent-exposed residues available for interferon beta receptor interactions, and to retain amino acids involved in intramolecular bonds. A panel of fifteen alanine scanning mutations were designed that replaced between two and eight residues along distinct regions of each of the helices (A (A1 (SEQ ID NO:26), A2 (SEQ ID NO:27)), B (B1(SEQ ID NO:31), B2(SEQ ID NO:32), C (C1 (SEQ ID NO:33), C2 (SEQ ID NO:34)), D (SEQ ID NO:37), E (SEQ ID NO:40)) and loops (AB1(SEQ ID NO:28), AB2 (SEQ ID NO:29), AB3 (SEQ ID NO:30), CD1 (SEQ ID NO:35), CD2 (SEQ ID NO:36), DE1 (SEQ ID NO:38), DE2 (SEQ ID NO:39) of interferon-beta-1a (SEQ ID NO:25). See Example 1.

An amino-terminal histidine tag ("his" tag) was included for affinity purification of mammalian cell expressed mutants (FIG. 10 and SEQ ID NOS: 1 and 2 for the cDNA and deduced amino acid sequences, respectively) Functional consequences of these mutations are assessed in antiviral and antiproliferation assays. A non-radioactive binding assay was developed to analyze these mutants for their binding to the interferon beta surface cell receptor (IFNAR½ cell surface receptor). In addition, an ELISA-based assay employing an IFNAR2-ectodomain/Ig fusion protein to bind interferon was used to map interactions of surfaces between interferon-beta-1a and IFNAR2 (See Example 1). These mutational analyses demonstrated that N- and C-termini lie in a portion of the interferon-beta molecule not important for receptor binding or biological function.

The mutants are further variants of the interferon beta 1a moiety of the invention that may be particularly useful inasmuch as they display novel properties not found in the wild type interferon-beta-1a (See Example 1). We have identified three types of effects that were caused by targeted mutagenesis. These effects may be advantageous for interferon drug development under certain circumstances. The three types of effect are as follows: (a) mutants with higher antiviral activity that of his-wild-type interferon-beta-1a (e.g. mutant C1); (b) mutants which display activity in both antiviral and antiproliferation assays, but for which antiproliferation activity is disproportionately low with respect to antiviral activity, compared to his-wild-type interferon-beta-1a (e.g., mutants C1, D and DE1); and (c) functional antagonists (e.g., A1, B2, CD2 and DE1), which show antiviral and antiproliferative activities that are disproportionately low with respect to receptor binding, compared to his-wild-type interferon-beta-1a.

The Polymer Moiety

Within the broad scope of the present invention, a single polymer molecule may be employed for conjugation with an interferon-beta 1a, although it is also contemplated that more than one polymer molecule can be attached as well. Conjugated interferon-beta 1a compositions of the invention may find utility in both in vivo as well as non-in vivo applications. Additionally, it will be recognized that the conjugating polymer may utilize any other groups, moieties, or other conjugated species, as appropriate to the end use application. By way of example, it may be useful in some applications to covalently bond to the polymer a functional moiety imparting UV-degradation resistance, or antioxidation, or other properties or characteristics to the polymer. As a further example, it may be advantageous in some applications to functionalize the polymer to render it reactive or cross-linkable in character, to enhance various properties or characterisics of the overall conjugated material. Accordingly, the polymer may contain any functionality, repeating groups, linkages, or other constitutent structures which do not preclude the efficacy of the conjugated interferon-beta 1a composition for its intended purpose. Other objectives and advantages of the present invention will be more fully apparent from the ensuing disclosure and appended claims.

Illustrative polymers that may usefully be employed to achieve these desirable characteristics are described herein below in exemplary reaction schemes. In covalently bonded peptide applications, the polymer may be functionalized and then coupled to free amino acid(s) of the peptide(s) to form labile bonds.

The interferon-beta-1a is conjugated most preferably via a terminal reactive group on the polymer although conjugations can also be branched from the non-terminal reactive groups. The polymer with the reactive group(s) is designated herein as "activated polymer". The reactive group selectively reacts with free amino or other reactive groups on the protein. The activated polymer(s) are reacted so that attachment may occur at any available interferon-beta-1a amino group such as the alpha amino groups or the epsilon-amino groups of lysines. Free carboxylic groups, suitably activated carbonyl groups, hydroxyl, guanidyl, oxidized carbohydrate moieties and mercapto groups of the interferon-beta-1a (if available) can also be used as attachment sites.

Although the polymer may be attached anywhere on the interferon-beta 1a molecule, the most preferred site for polymer coupling is the N-terminus of the interferon-beta-1a. Secondary site(s) are at or near the C-terminus and through sugar moieties. Thus, the invention contemplates as its most preferred embodiments: (i) N-terminally coupled polymer conjugates of interferon-beta-1a; (ii) C-terminally coupled polymer conjugates of interferon-beta-1a; (iii) sugar-coupled conjugates of polymer conjugates; (iv) as well as N-, C- and sugar-coupled polymer conjugates of interferon-beta-1a fusion proteins.

Generally from about 1.0 to about 10 moles of activated polymer per mole of protein, depending on protein concentration, is employed. The final amount is a balance between maximizing the extent of the reaction while minimizing non-specific modifications of the product and, at the same time, defining chemistries that will maintain optimum activity, while at the same time optimizing, if possible, the half-life of the protein. Preferably, at least about 50% of the biological activity of the protein is retained, and most preferably 100% is retained.

The reactions may take place by any suitable method used for reacting biologically active materials with inert polymers, preferably at about pH 5–7 if the reactive groups are on the alpha amino group at the N-terminus. Generally the process involves preparing an activated polymer (that may have at least one terminal hydroxyl group) and thereafter reacting the protein with the activated polymer to produce the soluble protein suitable for formulation. The above modification reaction can be performed by several methods, which may involve one or more steps.

As mentioned above, the most preferred embodiments of the invention utilize the N-terminal end of interferon-beta-1a as the linkage to the polymer. Suitable methods are available to selectively obtain an N-terminally modified interferon-beta-1a. One method is exemplified by a reductive alkylation method which exploits differential reactivity of different types of primary amino groups (the epsilon amino groups on the lysine versus the amino groups on the N-terminal methionine) available for derivatization on interferon-beta-1a. Under the appropriate selection conditions, substantially selective derivatization of interferon-beta-1a at its N-terminus with a carbonyl group containing polymer can be achieved. The reaction is performed at a pH which allows one to take advantage of the pKa differences between the epsilon-amino groups of the lysine residues and that of the alpha-amino group of the N-terminal residue of interferon-beta-1a. This type of chemistry is well known to persons with ordinary skill in the art.

We used a reaction scheme in which this selectivity is maintained by performing reactions at low pH (generally 5–6) under conditions where a PEG-aldehyde polymer is reacted with interferon-beta-1a in the presence of sodium cyanoborohydride. This results, after purification of the PEG-interferon-beta-1a and analysis with SDS-PAGE, MALDI mass spectrometry and peptide sequencing/mapping, resulted in an interferon-beta-1a whose N-terminus is specifically targeted by the PEG moiety.

The crystal structure of interferon-beta-1a us such that the N- and C-termini are located close to each other (see Karpusas et al., 1997, Proc. Natl. Acad. Sci. 94: 11813–11818). Thus, modifications of the C-terminal end of interferon-beta-1a should also have minimal effect on activity. While there is no simple chemical strategy for targeting a polyalkylene glycol polymer such as PEG to the C-terminus, it would be straightforward to genetically engineer a site that can be used to target the polymer moiety. For example, incorporation of a Cys at a site that is at or near the C-terminus would allow specific modification using a maleimide, vinylsulfone or haloacetate—activated polyalkylene glycol (e.g., PEG). These derivatives can be used specifically for modification of the engineered cysteines due to the high selectively of these reagents for Cys. Other strategies such as incorporation of a histidine tag which can be targeted (Fancy et al., (1996) Chem. & Biol. 3: 551) or an additional glycosylation site, represent other alternatives for modifying the C-terminus of interferon-beta-1a.

The glycan on the interferon-beta-1a is also in a position that would allow further modification without altering activity. Methods for targeting sugars as sites for chemical modification are also well known and therefore it is likely that a polyalkylene glycol polymer can be added directly and specifically to sugars on interferon-beta-1a that have been activated through oxidation. For example, a polyethyleneglycol-hydrazide can be generated which forms relatively stable hydrazone linkages by condensation with aldehydes and ketones. This property has been used for modification of proteins through oxidized oligosaccharide linkages. See Andresz, H. et al., (1978), Makromol. Chem. 179: 301. In particular, treatment of PEG-carboxymethyl hydrazide with nitrite produces PEG-carboxymethyl azide which is an electrophilically active group reactive toward amino groups. This reaction can be used to prepare polyalkylene glycol-modified proteins as well. See, U.S. Pat. Nos. 4,101,380 and 4,179,337.

We had previously discovered that thiol linker-mediated chemistry could further facilitate cross-linking of proteins. In particular, we generated homotypic multimers of LFA-3 and CD4 using a procedure such as generating reactive aldehydes on carbohydrate moieties with sodium periodate, forming cystamine conjugates through the aldehydes and inducing cross-linking via the thiol groups on the cystamines. See Pepinsky, B. et al., (1991), J. Biol. Chem., 266: 18244–18249 and Chen, L. L. et al., (1991) J. Biol. Chem., 266: 18237–18243. Therefore, we envision that this type of chemistry would also be appropriate for modification with polyalkylene glycol polymers where a linker is incorporated into the sugar and the polyalkylene glycol polymer is attached to the linker. While aminothiol or hydrazine-containing linkers will allow for addition of a single polymer group, the structure of the linker can be varied so that multiple polymers are added and/or that the spatial orientation of the polymer with respect to the interferon-beta-1a is changed.

In the practice of the present invention, polyalkylene glycol residues of C1–C4 alkyl polyalkylene glycols, preferably polyethylene glycol (PEG), or poly(oxy)alkylene glycol residues of such glycols are advantageously incorporated in the polymer systems of interest. Thus, the polymer to which the protein is attached can be a homopolymer of polyethylene glycol (PEG) or is a polyoxyethylated polyol, provided in all cases that the polymer is soluble in water at room temperature. Non-limiting examples of such polymers include polyalkylene oxide homopolymers such as PEG or polypropylene glycols, polyoxyethylenated glycols, copolymers thereof and block copolymers thereof, provided that the water solubility of the block copolymer is maintained. Examples of polyoxyethylated polyols include, for example, polyoxyethylated glycerol, polyoxyethylated sorbitol, polyoxyethylated glucose, or the like. The glycerol backbone of polyoxyethylated glycerol is the same backbone occurring naturally in, for example, animals and humans in mono-, di-, and triglycerides. Therefore, this branching would not necessarily be seen as a foreign agent in the body.

As an alternative to polyalkylene oxides, dextran, polyvinyl pyrrolidones, polyacrylamides, polyvinyl alcohols, carbohydrate-based polymers and the like may be used. Those of ordinary skill in the art will recognize that the foregoing list is merely illustrative and that all polymer materials having the qualities described herein are contemplated.

The polymer need not have any particular molecular weight, but it is preferred that the molecular weight be between about 300 and 100,000, more preferably between 10,000 and 40,000. In particular, sizes of 20,000 or more are best at preventing protein loss due to filtration in the kidneys.

Polyalkylene glycol derivatization has a number of advantageous properties in the formulation of polymer-interferon-beta 1a conjugates in the practice of the present invention, as associated with the following properties of polyalkylene glycol derivatives: improvement of aqueous solubility, while at the same time eliciting no antigenic or immunogenic response; high degrees of biocompatibility; absence of in vivo biodegradation of the polyalkylene glycol derivatives; and ease of excretion by living organisms.

Moreover, in another aspect of the invention, one can utilize interferon-beta 1a covalently bonded to the polymer component in which the nature of the conjugation involves cleavable covalent chemical bonds. This allows for control in terms of the time course over which the polymer may be cleaved from the interferon-beta 1a. This covalent bond between the interferon-beta-1a drug and the polymer may be cleaved by chemical or enzymatic reaction. The polymer-interferon-beta-1a product retains an acceptable amount of activity. Concurrently, portions of polyethylene glycol are present in the conjugating polymer to endow the polymer-interferon-beta-1a conjugate with high aqueous solubility and prolonged blood circulation capability. As a result of these improved characteristics the invention contemplates parenteral, nasal, and oral delivery of both the active polymer-interferon-beta-1a species and, following hydrolytic cleavage, bioavailability of the interferon-beta-1a per se, in in vivo applications.

It is to be understood that the reaction schemes described herein are provided for the purposes of illustration only and are not to be limiting with respect to the reactions and structures which may be utilized in the modification of the interferon-beta-1a, e.g., to achieve solubility, stabilization, and cell membrane affinity for parenteral and oral administration. The reaction of the polymer with the interferon-beta 1a to obtain the most preferred N-terminal conjugated products is readily carried out using a wide variety of reaction schemes. The activity and stability of the interferon-beta-1a conjugates can be varied in several ways, by using a polymer of different molecular size. Solubilities of the conjugates can be varied by changing the proportion and size of the polyethylene glycol fragment incorporated in the polymer composition.

Utilities

The unique property of polyalkylene glycol-derived polymers of value for therapeutic applications of the present invention is their general biocompatibility. The polymers have various water solubility properties and are not toxic. They are believed non-immunogenic and non-antigenic and do not interfere with the biological activities of the interferon-beta-1a moiety when conjugated under the conditions described herein. They have long circulation in the blood and are easily excreted from living organisms.

The products of the present invention have been found useful in sustaining the half life of therapeutic interferon-beta 1a, and may for example be prepared for therapeutic administration by dissolving in water or acceptable liquid medium. Administration is by either the parenteral, aerosol, or oral route. Fine colloidal suspensions may be prepared for parenteral administration to produce a depot effect, or by the oral route while aerosol formulation may be liquid or dry powder in nature. In the dry, lyophilized state or in solution formulations, the interferon-beta-1a-polymer conjugates of the present invention should have good storage stability. The thermal stability of conjugated interferon-beta-1a (Example 3) is advantageous in powder formulation processes that have a dehydration step. See, e.g., PCT/US/95/06008 ("Methods and Compositions for Dry Powder of Interferons").

The therapeutic polymer conjugates of the present invention may be utilized for the prophylaxis or treatment of any condition or disease state for which the interferon-beta-1a constituent is efficacious. In addition, the polymer-based conjugates of the present invention may be utilized in diagnosis of constituents, conditions, or disease states in biological systems or specimens, as well as for diagnosis purposes in non-physiological systems.

In therapeutic usage, the present invention contemplates a method of treating an animal subject having or latently susceptible to such condition(s) or disease state(s) and in need of such treatment, comprising administering to such animal an effective amount of a polymer conjugate of the present invention which is therapeutically effective for said condition or disease state. Subjects to be treated by the polymer conjugates of the present invention include mammalian subjects and most preferably human subjects.

Depending on the specific condition or disease state to be combated, animal subjects may be administered polymer conjugates of the invention at any suitable therapeutically effective and safe dosage, as may readily be determined within the skill of the art, and without undue experimentation. Because of the species barriers of Type I interferons, it may be necessary to generate interferon-polymer conjugates as described herein with interferons from the appropriate species.

The anti-cell proliferative activity of interferon-beta-1a is well known. In particular, certain of the interferon-beta-1a polymer conjugates described herein are useful for treating tumors and cancers such as osteogenic sarcoma, lymphoma, acute lymphocytic leukemia, breast carcinoma, melanoma and nasopharyngeal carcinoma, as well as autoimmune conditions such as fibrosis, lupus and multiple sclerosis. It is further expected that the anti-viral activity exhibited by the conjugated proteins, in particular certain of the interferon-beta-1a mutein conjugates described herein, may be used in the treatment of viral diseases, such as ECM infection, influenza, and other respiratory tract infections, rabies, and hepatitis. It is also expected that immunomodulatory activities of interferon-beta-1a exhibited by the conjugated proteins described herein, may be used in the treatment of autoimmune and inflammatory diseases, such as fibrosis, multiple sclerosis. The ability of interferons to inhibit formation of new blood vessels (i.e., inhibit angiogenesis and neovascularization) enables conjugates of the invention to be used to treat angiogenic diseases such as diabetic retinopathy, retinopathy of prematurity, macular degeneration, corneal graft rejection, neovascular glaucoma, retrolental fibroplasia, rubeosis and Osler-Webber Syndrome.

Moreover, the antiendothelial activity of interferon has been known for some time and one potential mechanism of interferon action may be to interfere with endothelial cell activity by inhibiting the production or efficacy of angiogenic factors produced by tumor cells. Some vascular tumors, such as hemangiomas, are particularly sensitive to treatment with interferon. Treatment with interferon-alpha is the only documented treatment for this disease. It is expected that treatment with the interferon-beta-1a conjugates of the invention will offer subtantial pharmaceutical benefits in terms of pharmacokinetics and pharmacodynamics, since the conjugate is expected to remain in the vasculature for a longer period of time than non-conjugated interferons, thus leading to more efficient and effective therapy for use as an anti-angiogenic agent. See Example 8.

The polymer-interferon-beta-1a conjugates of the invention may be administered per se as well as in the form of pharmaceutically acceptable esters, salts, and other physiologically functional derivatives thereof. In such pharmaceutical and medicament formulations, the interferon-beta-1a preferably is utilized together with one or more pharmaceutically acceptable carrier(s) and optionally any other therapeutic ingredients. The carrier(s) must be pharmaceutically acceptable in the sense of being compatible with the other ingredients of the formulation and not unduly deleterious to the recipient thereof. The interferon-beta-1a is provided in an amount effective to achieve the desired pharmacological effect, as described above, and in a quantity appropriate to achieve the desired daily dose.

The formulations include those suitable for parenteral as well as non-parenteral administration, and specific administration modalities include oral, rectal, buccal, topical, nasal, ophthalmic, subcutaneous, intramuscular, intravenous, transdermal, intrathecal, intra-articular, intra-arterial, sub-arachnoid, bronchial, lymphatic, vaginal, and intra-uterine administration. Formulations suitable for oral, nasal, and parenteral administration are preferred.

When the interferon-beta-1a is utilized in a formulation comprising a liquid solution, the formulation advantageously may be administered orally or parenterally. When the interferon-beta-1a is employed in a liquid suspension formulation or as a powder in a biocompatible carrier formulation, the formulation may be advantageously administered orally, rectally, or bronchially.

When the interferon-beta-1a is utilized directly in the form of a powdered solid, the interferon-beta-1a may advantageously be administered orally. Alternatively, it may be administered nasally or bronchially, via nebulization of the powder in a carrier gas, to form a gaseous dispersion of the powder which is inspired by the patient from a breathing circuit comprising a suitable nebulizer device.

The formulations comprising the polymer conjugates of the present invention may conveniently be presented in unit dosage forms and may be prepared by any of the methods well known in the art of pharmacy. Such methods generally include the step of bringing the active ingredient(s) into association with a carrier which constitutes one or more accessory ingredients. Typically, the formulations are prepared by uniformly and intimately bringing the active ingredient(s) into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered polymer conjugates with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active conjugate, which preferably is isotonic with the blood of the recipient (e.g., physiological saline solution). Such formulations may include suspending agents and thickening agents or other microparticulate systems which are designed to target the compound to blood components or one or more organs. The formulations may be presented in unit-dose or multi-dose form.

Nasal spray formulations comprise purified aqueous solutions of the active conjugate with preservative agents and isotonic agents. Such formulations are preferably adjusted to a pH and isotonic state compatible with the nasal mucus membranes.

Formulations for rectal administration may be presented as a suppository with a suitable carrier such as cocoa butter, hydrogenated fats, or hydrogenated fatty carboxylic acid.

Ophthalmic formulations such as eye drops are prepared by a similar method to the nasal spray, except that the pH and isotonic factors are preferably adjusted to match that of the eye.

Topical formulations comprise the conjugates of the invention dissolved or suspended in one or more media, such as mineral oil, petroleum, polyhydroxy alcohols, or other bases used for topical pharmaceutical formulations.

In addition to the aforementioned ingredients, the formulations of this invention may further include one or more accessory ingredient(s) selected from diluents, buffers, flavoring agents, disintegrants, surface active agents, thickeners, lubricants, preservatives (including antioxidants), and the like.

Accordingly, the present invention contemplates the provision of suitable polymers for in vitro stabilization of interferon-beta 1a in solution, as a preferred illustrative application of non-therapeutic application. The polymers may be employed for example to increase the thermal stability and enzymic degradation resistance of the interferon-beta 1a. Enhancement of the thermal stability characteristic of the interferon-beta-1a via conjugation in the manner of the present invention provides a means of improving shelf life, room temperature stability, and robustness of research reagents and kits.

The following Examples are provided to illustrate the present invention, and should not be construed as limiting thereof. In particular, it will be understood that the in vivo, animal experiments described herein may be varied, so that other modifications and variations of the basic methodology are possible. For example, in Example 5, one of ordinary skill in the art could use other neopterin assays or could alter the number and kind of primate used. These modifications and variations to the Examples are to be regarded as being within the spirit and scope of the invention.

EXAMPLE 1

Structure/activity Studies of Human Interferon-beta-1a Using Alanine/serine Substitution Mutations
Analysis of Receptor Binding Sites and Functional Domains A. Overview An extensive mutational analysis of human interferon-beta-1a (IFN-beta-1a) was undertaken with the aims of mapping residues required for activity and receptor binding. The availability of the 3-D crystal structure of human IFN-beta (Karpusas, M. et al. 1997, Proc. Natl. Acad. Sci. 94: 11813–11818) allowed us to identify for alanine (or serine) substitutions the solvent-exposed residues available for receptor interactions, and to retain amino acids involved in intramolecular bonds. A panel of 15 alanine substitution mutations were designed that replaced between 2 and 8 residues along distinct regions of each of the helices (A, B, C, D, E) and loops (AB, CD, DE). An amino-terminal histidine tag comprising six histidine residues was included for affinity purification, as well as an enterokinase cleavage site for removal of the amino-terminal extension. The resulting interferons are referred to as "his tagged-interferon (IFN)-beta" or "His-interferon-beta" or "His$_6$-interferon-beta" and the like.

Various mutant his tagged-IFN-beta expression plasmids were constructed using a wild type IFN-beta gene construct as a template for mutagenesis. The mutagenesis strategy involved first introducing unique restriction enzyme cleavage sites throughout the wild type his tagged-IFN beta gene, then replacing distinct DNA sequences between the chosen restriction sites with synthetic oligonucleotide duplexes, which encoded the alanine (or serine) substitution mutations. Finally, the mutant IFN genes were subcloned into a plasmid which directed mammalian cell expression in a human 293 kidney cell line.

Functional consequences of these mutations were assessed in antiviral and antiproliferation assays. A non-radioactive IFN binding assay was developed to analyze these mutants in their binding to the surface receptor ("IFNAR½ complex") of human Daudi Burkitt's lymphoma cells. In addition, an assay to map interaction surfaces between his-IFN-beta mutants and IFNAR2 was developed that employed a IFNAR2/Ig fusion protein, comprised of the IFN receptor protein IFNAR2 extracellular domain fused to the hinge, CH2 and CH3 domains of human IgG1.

1. Creation of an interferon beta gene as a template for mutagenesis

Our strategy to generate IFN-beta alanine (or serine) substituted mutants was to first create a modified IFN-beta gene, which encoded the wild type protein but which carried unique restriction enzyme cleavage sites scattered across the gene. The unique sites were used to exchange wild type sequences for synthetic oligonucleotide duplexes, which encode the mutated codons. In order to obtain an human IFN-beta-1a expression cassette suitable for creation of mutant genes, the IFN-beta cDNA (GenBank accession #E00029) was amplified by PCR. An initial cloning of the IFN-beta gene into plasmid pMJB107, a derivative of pACYC184, see Rose, et. al., 1988, Nucleic Acids Res. 16 (1) 355) was necessary in order to perform site-directed mutagenesis of the gene in a plasmid that lacked the specific restriction sites which would be generated through the mutagenesis.

The PCR primers used to subclone the coding sequences of the human IFN-beta gene also allowed us to introduce an enterokinase cleavage site upstream and in frame with the IFN-beta gene incorporating flanking restriction enzyme cleavage sites (NotI and BspEI) that allowed excision of the fragment B DNA.

To create a plasmid vector that carried the VCAM-1 signal sequence, his tag and interferon-beta gene we performed a three-way ligation using gel purified DNA fragments from plasmid vector pMJB 107 (NotI and XhoI cleaved), PCR fragment A (BspEI and XhoI cleaved) and fragment B (NotI and BspEI cleaved). The ligated plasmid was used to transform either JA221 or XL1-Blue E. coli cells and ampicillin resistant colonies were picked and tested for inserts by restriction map analysis. Maxiprep DNA was made and the sequence of the insert was verified by DNA sequencing. The resulting construct was called pCMG260.

2. Creation of alanine substitution mutants of human interferon-beta in pCMG260

The plasmid pCMG260 was used as a template for multiple rounds of mutagenesis (U.S.E. Site Directed Mutagenesis Kit (Boehringer-Mannheim), which introduced unique restriction cleavage sites into positions along the IFN-beta protein coding sequence but did not change the resulting sequence of the protein. The mutagenized plasmids were used to transform either the JA221 or XL1-Blue strains of E. coli and recombinant colonies selected for chloramphenicol resistance. Chloramphenicol resistant colonies were further tested for the presence of the desired unique restriction enzyme site by DNA restriction mapping analysis. The resulting IFN-beta plasmid, pCMG275.8, contained the full set of unique restriction enzyme cleavage sites and the DNA sequence of the gene was verified. The full DNA sequence (SEQ ID NO: 1) of the modified, his-tagged interferon beta gene, together with the protein coding sequence (SEQ ID NO: 2), are given in FIG. 10.

The full set of alanine substitution mutations are depicted in Table 1 (below). The names of the mutants specify the structural regions (helices and loops) in which the mutations were introduced. The entire panel of alanine (serine) substitutions results in mutation of 65 of the 165 amino acids of human IFN-beta.

The panel of mutants was created from pCMG275.8 by replacing segments of DNA between the unique restriction

```
(5' PCR primer   5'TTCTCCGGAGACGATGATGACAAGATGAGCTACAACTT      (SEQ ID NO: 3: "BET-021", and
                 GCTTGGATTCCTACAAAGAAGC-3'

3' PCR primer    5'-GCCGCTCGAGTTATCAGTTTCGGAGGTAACCTGTAAGTC-3'   (SEQ ID NO: 4: "BET-022")
``` and flanking restriction enzyme sites (BspEI and Xho I) useful for cloning into plasmid pMJB107 sites. The resulting DNA is refererred to as PCR fragment A.

An efficient signal sequence from the human vascular cell adhesion molecule-1 (VCAM-1) signal sequence and a six histidine tag were introduced into the final construct from a second DNA fragment created from pDSW247 (fragment B). Plasmid pDSW247 is a derivative of pCEP4 (Invitrogen, Carlsbad, Calif.) from which the EBNA-1 gene has been deleted, and which carries the VCAM-1 signal sequence (VCAMss) fused upstream and in frame with a six histidine tag. The PCR primers that were used to generate the VCAMss-1/histidine tag cassette moiety were KID-369 sites with synthetic oligonucleotide duplexes, which carried the genetic coding information depicted in Table 2 (see below). To create the various alanine substitution mutant plasmids gel purified pCMG275.8 vector (cleaved with the appropriate restriction enzyme, as indicated on the list below for each IFN-beta structural region) and oligonucleotide duplexes (coding strand sequences are shown in Table 2) were ligated together. The ligation mixtures were used to transform the JA221 strain of E. coli and recombinant colonies selected for ampicillin resistance. Ampicillin resistant colonies were tested for the presence of the insertion of the mutations by screening for appropriate restriction enzyme sites. For two mutants (A2 and CD2), the cloning

```
(5' PCR primer        5'-AGCTTCCGGGGGCCATCATCATCATCATCATAGCT-3':  SEQ ID NO: 5) and KTD-421 (3' PCR primer 5'-CCGGAGCTATGATGATGATGATGATGGCCCCCGGA-3':  SEQ ID NO: 6)
``` strategy entailed using two duplexes of synthetic oligonucleotides (shown in Table 2), which carry complementary overhanging ends to allow them to ligate to each other and the vector-IFN-beta backbone in a three-way ligation. The following list illustrates the sites which were used to clone the mutated oligonucleotides from Table 2. The cloning scheme (subsection B) shows the positions of these unique sites on the interferon beta gene.

TABLE 1

Positions of alanine substitution mutations of HU IFN-β

```
         1        10         20        30        40        50
         |.  ..  .|.   .. ..| ..     ..|. ..  .. .|   . .....|...
IFN-β    MSYNLLGFLQRSSNFQCQKLLWQLNGRLEYCLKDRMNFDIPEEIKQLQQFQKE
A1       -A-AA--A--A------------------------------------------
A2       --------------AA-AA--AA------------------------------
AB1      --------------------------AAA-AA---------------------
AB2      ----------------------------------AA-A--A------------
AB3      --------------------------------------------AAAAA-AAA
         |______helix A_______||_______AB loop__________|

60        70        80        90       100
               |    .  .. | ...    |..  ..  .| .    .   .|. ..   ...
IFN-β    DAALTIYEMLQNIFAIFRQDSSSTGWNETIVENLLANVYHQINHLKTVEEKLEKE
B1       ----------A--AS-----------------------------------------
B2       -----------------AAA------------------------------------
C1       ---------------------------AS--AA--S--------------------
C2       --------------------------------------A---A--AA---------
CD1      -------------------------------------------------AA--AAA
         |_______helix B_||____________________||_CD loop__

110       120       130       140       150       160
         |.. .   . .|        . |.. . .. .|.      . | .   .  .|
IFN-β    DFTRGALMSSHLKRYYGRILHYLKAKEYSHCAWTIVRVEILRNFYRINRLTGYLRN
CD2      AA-A--A--A-----------------------------------------------
D        ------------------A-AA--A--------------------------------
DE1      --------------------------AA-----------------------------
DE2      -----------------------------AA--------------------------
E        --------------------------------------A---A--A--A--------
         CD loop_||___helix D___|    |_____helix E_________|
```

The line designated IFN-β shows the wild type human IFN-β sequence. Alanine or serine substitutions of the IFN-β residues are shown for each of the mutants and dashes, below relevant regions, indicate wild type sequences. The helices and loop structures are indicated as solid lines below the mutants. The DE loop spans the gap between the D and E helices. Two additional alanine substitution mutants (H93A, H97A and H121A) were generated and analyzed in antiviral assays to assess the effects of mutating these histidines, which chelate zinc in the crustal structure dimer. Both of these mutants retained full wild type activity in antiviral assays, suggesting that zinc-mediated dimer formation is not important for IFN-β activity.

TABLE 2

| | | |
|---|---|---|
| A1 | SEQ ID NO: 7<br>BET-053 | CCGGAGACGATGATGACAAGATGGCTTACGCCGCTCTTGGAOCCCTACAAGC<br>TTCTAGCAATTTTCAGTGTCAGAAGCTCCTGTGGC |
| A2 | SEQ ID NO: 8<br>BET-039 | CATCTAGCAATGCTGCCTGTGCTGCCCTCCTGGCTGCCTTGAATGGGAGGCTT<br>GAATACT |
| | SEQ ID NO: 9<br>BET-041 | GCCTCAAGGACAGGATGAACTTTGACATCCCTGAGGAGATTAAGCAGCTGCA |
| AB<br>1 | SEQ ID NO: 10<br>BET-080 | AATTGAATGGGAGGGCTGCAGCTTGCGCTGCAGACAGGATGAACTTTGACATCC<br>CTGAGGAGATTAAGCAGCTGCA |
| AB<br>2 | SEQ ID NO: 11<br>BET-082 | AATTGAATGGGAGGCTTGAATACTGCCTCAAGGACAGGGCTGCATTTGCTATC<br>CCTGCAGAGATTAAGCAGCTGCA |

TABLE 2-continued

| | | | |
|---|---|---|---|
| AB 3 | SEQ ID NO: 12 BET-084 | AATTGAATGGGAGGCTTGAATACTGCCTCAAGGACAGGATGAACTTTGACA | |
| | SEQ ID NO: 13 BET-086 | TCCCTGAGGAGATTGCTGCAGCTGCAGCTTTCGCTGCAGCTGA | |
| B1 | SEQ ID NO: 14 BET-110 | CGCCGCGTTGACCATCTATGAGATGCTCGCTAACATCGCTAGCATTTTCA GACAAGATTCATCTAGCACTGGCTGGAA | |
| B2 | SEQ ID NO: 15 BET-112 | CGCCGCATTGACCATCTATGAGATGCTCCAGAACATCTTTGCTATTTTCGC TGCAGCTTCATCTAGCACTGGCTGGAA | |
| C1 | SEQ ID NO: 16 BET-114 | GCAATGCTTCAATTGTTGCTGCACTCCTGAGCAATGTCTATCATCAGATAA ACCATCTGAACACACTTCTAG | |
| C2 | SEQ ID NO: 17 BET-092 | GGAATGACACCATTGTTGAGAACCTCCTGGCTAATGTCGCTCATCAGATAG CACATCTCCCTCCAGTTCTAG | |
| CD 1 | SEQ ID NO: 18 BET- 094 | CTAGCTGCAAAACTGGCTGCAGCTGATTTCACCAGGGGAAAACT | |
| CD 2 | SEQ ID NO: 19 BET- 096 | CTAGAAGAAAAACTGGAGAAAGAAGCAGCTACCGCTGGAAAAGCAATGA GCGCGCTGCACCTGAAAAGA | |
| | SEQ ID NO: 20 BET-106 | TATTATGGGAGGATTCTGCATTACCTGAAGGCCAAGGAGTACTCACACTGT | |
| D1 | SEQ ID NO: 21 BET-108 | CATGAGCAGTCTGCACCTGAAAAGATATTATCGGGCAATTGCTGCATACCTG GCAGCCAACGACTACTCACACTGT | |
| DE 1 | SEQ ID NO: 22 BET-116 | CATGAGCAGTCTGCACCTGAAAAGATATTATGGGAGGATTCTGCATTACCTG AAGGCCGCTGCATACTCACACTGTGCCTGGACGAT | |
| DE 2 | SEQ ID NO: 23 BET-118 | CATGAGCAGTCTGCACCTGAAAAGATATTATGGGAGGATTCTGCATTACCTGA AGGCAAAGGAGTACGCTGCATGTGCCTGGACGAT | |
| E1 | SEQ ID NO: 24 BET-104 | CGTCAGAGCTGAATCCTAGCAAACTTTGCATTCATTGCAAGACTTACAG | |

B. Construction of EBNA 293 Expression Plasmids

The wild type and mutant IFN-beta genes, fused to the VCAM-1 signal sequence, his tag and enterokinase cleavage site, were gel purified as 761 base pair NotI and BamHI restriction fragments. The purified genes were subcloned into NotI and BamHI cleaved plasmid vector pDSW247, as depicted in the schematic. Plasmid pDSW247 is an expression vector for transient expression of protein in human EBNA 293 kidney cells (Invitrogen, Carlsbad, Calif.). It contains the cytomegalovirus early gene promoter and EBV regulatory elements which are required for high level gene expression in that system, as well as selectable markers for E. coli (ampicillin resistance) and EBNA 293 cells (hygromycin resistance) as seen in the cloning strategy schematic (below). The ligated plasmids were used to transform either JA221 or XL1-Blue E. coli cells and ampicillin resistant colonies were picked and tested for inserts by restriction map analysis. Maxiprep DNA was made and the sequence of the inserts was verified by DNA sequencing. Positive clones displaying the desired mutagenized sequences were used to transfect human EBNA 293 kidney cells as described below.

C. Expression and Quantitation of IFN-beta-1a Alanine Substitution Mutants

The human EBNA 293 cells (Invitrogen, Carlsbad, Calif., Chittenden, T. (1989) J. Virol. 63: 3016–3025) were maintained as subconfluent cultures in Dulbecco's Modified Eagle's media supplemented with 10% fetal bovine serum, 2 mM glutamine and 250 μg/ml Geneticin (Life Technologies, Gaithersburg, Md.). The pDSW247 expression plasmids were transiently transfected into EBNA 293 cells using the lipofectamine protocol (Gibco/BRL, Life Technologies). Conditioned media was harvested 3–4 days posttransfection, cell debris was removed by centrifugation, and the his-IFN-beta concentration was quantitated by ELISA.

The ELISA assay was performed using polyclonal rabbit antibodies (protein A purified IgG, antibodies had been raised to purified human IFN-beta-1a) to coat 96-well ELISA plates and a biotinylated form of the same polyclonal rabbit IgG was used as a secondary reagent to allow interferon detection using streptavidin-linked horseradish peroxidase (HRP: Jackson ImmunoResearch, W. Grove, Pa.). A dilution series of interferon-beta-1a was used to generate standard concentration curves. The his-IFN-beta containing conditioned media from the EBNA transfectants were diluted to obtain samples with concentrations ranging between 10 ng/ml and 0.3 ng/ml in the ELISA assay. To confirm the concentrations of the IFN-beta in media determined by ELISA, western blot analysis was performed. Reduced culture supernatants and IFN-beta-1a standards were subjected to SDS-PAGE on 10–20% gradient gels (Novex, San Diego, Calif.) and blotted onto PDVF membranes. Immunoreactive bands were detected with a rabbit polyclonal anti-IFN-beta-1a antiserum (#447, Biogen, Inc., a second antiserum that had been raised against IFN-beta-1a), followed by treatment with HRP-linked donkey anti-rabbit IgG (Jackson ImmunoResearch).

D. Assessing the Interferon-beta Mutants for Receptor Binding

Figure 1:
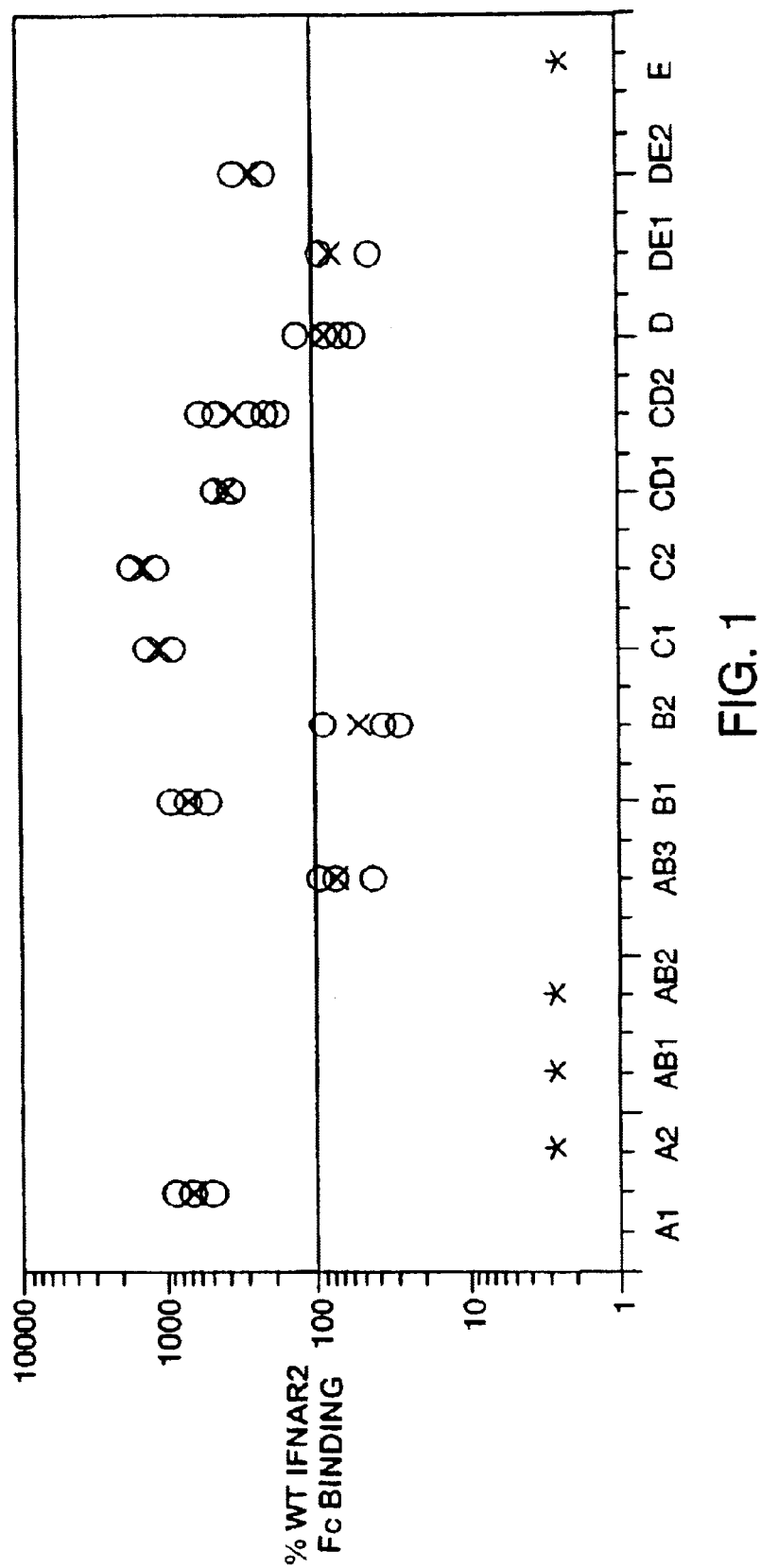
FIG. 1. Binding of alanine substituted interferon-beta-1a mutants to a dimeric fusion protein comprising the extracellular domain of the type I interferon receptor chain, IFNAR2/Ig (IFNAR2 ectodomain fused to the human IgG1 constant domain.

The receptor binding properties of the Interferon-beta mutants described in C were assessed using two different binding assays. One assay measured binding of the interferon-beta mutants to a fusion protein, IFNAR2/Ig, comprising the extracellular domain of the human IFNAR2 receptor chain fused to part of the constant region of a human IgG. IFNAR2-Fc was expressed in chinese hamster ovary (CHO) cells and purified by protein A sepharose affinity chromatography according to the instructions of the manufacturer (Pierce Chem. Co., Rockford, Ill., catalog #20334). The binding of interferon-beta mutants to IFNAR2-Fc was measured in an ELISA format assay. ELISA plates were prepared by coating flat-bottomed 96 well plates overnight at 4° C. with 50 µl/well of mouse anti-human IgG1 monoclonal antibody (CDG5-AA9, Biogen, Inc.) at 10 µg/ml in coating buffer (50 mM $NaHCO_3$, 0.2 mM $MgCl_2$, 0.2 mM $CaCl_2$, pH 9.6). Plates were washed twice with PBS containing 0.05% Tween-20, and blocked with 0.5% non-fat dry milk in PBS for 1 hour at room temperature. After two more washes, 50 µl of 1 µg/ml IFNAR2-Fc in 0.5% milk in PBS containing 0.05% Tween-20 was added to each well and incubated for 1 hour at room temperature, and the plates were then washed twice more. Binding of the interferon-beta mutants to IFNAR2-Fc was measured by adding 50 µl/well mutant interferon-beta in conditioned media, serially diluted in Dulbecco's Modified Eagle's Medium (DMEM) supplemented with 10% fetal bovine serum, and incubating for 2 hours at 4° C. Dilutions of interferon-beta mutant typically ranged from approximately 1 µM down to 10 pM. After washing, interferon-beta bound to the plates was detected by adding 50 µl/well of a cocktail consisting of a 1:1000 dilution of a rabbit polyclonal anti-interferon antibody (#447) plus horseradish peroxidase (HRP)-labelled donkey anti-rabbit IgG (Jackson ImmunoResearch), and incubating for 15 minutes at 4° C. After two washes, HRP substrate was added, and the plate was incubated at 4° C. before being read on an ELISA plate reader at an absorbance of 450 nm. Data were plotted as absorbance versus the concentration of mutant interferon-beta, and the affinity for the binding of the mutant interferon-beta to IFNAR2-Fc was determined by fitting the data to a simple hyperbolic binding equation. Results from these analyses are shown in FIG. 1, in which the binding affinity for each mutant, determined at least three independent experiments, is expressed as a percentage of that measured for $His_6$-wild-type interferon-beta-1a.

A second receptor binding assay was used to measure the affinity with which the interferon-beta mutants bound to Daudi cells expressing both receptor chains, IFNAR1 and IFNAR2, which together comprise the receptor for interferon-beta. This FACS-based assay used a blocking monoclonal antibody directed against the extracellular domain of IFNAR1, EA12 (Biogen, Inc.), to distinguish unoccupied (free) receptor from receptor to which interferon-beta was bound. Daudi cells (20 µl at $2.5 \times 10^7$ cells/ml) were placed in 96-well V-bottom ELISA plates, and incubated for 1 hour at 4° C. with various concentrations of interferon-beta mutant (20 µl in FACS buffer; 5% FBS, 0.1% $NaN_3$ in PBS). Desirable serial dilutions of interferon-beta mutants ranged from 0.5 µM down to 0.5 pM. To each well was added 100 ng of biotinylated murine anti-IFNAR1 monoclonal antibody EA12 (10 µl), and the plates incubated for an additional 2 minutes at room temperature before being washed twice with FACS buffer (4° C.). The cells were then incubated for 30 minutes at 4° C. with 50 µl/well of a 1:200 dilution of R-Phycoerythrin-conjugated streptavidin (Jackson ImmunoResearch), washed twice in FACS buffer, resuspended in 300 µl FACS buffer containing 0.5% paraformaldehyde, and transferred into 12×75 mm polystyrene tubes (Falcon 2052). The samples were then analyzed by flow cytometry on a FACScan (Becton Dickinson). Data were plotted as mean channel fluorescence intensity (MFCI) versus the concentration of interferon-beta mutant; binding affinities were defined as the concentration of interferon-beta mutant giving 50% inhibition of antibody staining. Each mutant was tested multiple times. FIG. 2 shows the receptor binding affinities for each interferon-beta mutant, determined by this method, expressed as a percentage of the affinity measured for $His_6$-wild-type interferon-beta-1a in each experiment.

E. Assessing the Interferon-beta Mutants for Function

The interferon-beta mutants were also tested for functional activity using in vitro assays for antiviral activity and for the ability of the interferon-beta to inhibit cell proliferation. A minimum of three antiviral assays, each with triplicate data points, were performed on each mutant. $His_6$-wild-type interferon-beta-1a was included as a reference in every experiment. The antiviral assays were performed by treating A549 human lung carcinoma cells (ATCC CCL 185) overnight with 2-fold serial dilutions of mutant interferon-beta at concentrations that spanned the range between full antiviral protection and no protection from viral cell killing. The following day, the cells were challenged for two days with encephalomyocarditis virus (ECMV) at a dilution that resulted in complete cell killing in the absence of interferon. Plates were then developed with the metabolic dye MTT (2,3-bis[2-Methoxy-4-nitro-5-sulfo-phenyl]-2H-tetrazolium-5-carboxyanilide) (M-5655, Sigma, St. Louis, Mo.). A stock solution of MTT was prepared at 5 mg/ml in PBS and sterile filtered, and 50 $\mu$l of this solution was diluted into cell cultures (100 $\mu$l per well). Following incubation at room temperature for 30–60 minutes, the MTT/media solution was discarded, cells were washed with 100 $\mu$l PBS, and finally the metabolized dye was solubilized in 100 $\mu$l 1.2N hydrochloric acid in 90% isopropanol. Viable cells (as evidenced by the presence of the dye) were quantified by absorbance at 450 nm. Data were analyzed by plotting absorbance against the concentration interferon-beta mutant, and the activity of each mutant was defined as the concentration at which 50% of the cells were killed. FIG. 3 shows the activity of each mutant expressed as a percentage of the activity measured for his tagged-wild-type interferon-beta-1a in each experiment.

Interferon-beta mutants were also assessed for function in an antiproliferation assay. Human Daudi Burkitt's lymphoma cells (ATCC # CCL 213) were seeded at $2\times10^5$ cells/ml in RPMI 1620 supplemented with 10% defined fetal calf serum (Hyclone, Logan Utah), and 2 mM L-glutamine. Each well also contained a given concentration of interferon-beta mutant in a final total volume of 100 $\mu$l of medium per well; the interferon-beta concentrations used were chosen to span the range from maximal inhibition of Daudi cell proliferation to no inhibition (i.e. full proliferation). Duplicate experimental points were used for each concentration of interferon-beta mutant tested, and a duplicate set of untreated cells was included in all experiments. Cells were incubated for two days at 37° C. in 5% $CO_2$ incubators, after which 1 $\mu$Ci per well of tritiated thymidine ((methyl-$^3$H) thymidine, Amersham TRK758) in 50 $\mu$l medium was added to each well, and incubated for a further 4 h. Cells were harvested using a LKB plate harvester, and incorporation of tritiated thymidine was measured using a LKB beta plate reader. Duplicate experimental values were averaged and the standard deviations determined. Data were plotted as mean counts per minute versus the concentration of interferon-beta mutant, and the activity of each mutant was defined as the concentration required to give 50% of the maximal observed growth inhibition. Multiple assays for each mutant were performed. FIG. 4 shows the results expressed as a percentage of the activity found for his tagged-wild-type interferon-beta-1a in each experiment.

F. Properties of the Interferon-Beta Mutants

Histidine tagged-wild-type interferon-beta-1a was found to have activities in the antiviral and antiproliferation assays that were each about 3-fold lower than the corresponding activities found for untagged wild-type interferon-beta-1a. Because all of the interferon-beta mutants A1–E contain the identical his tag sequence at their N-termini, the effects of the mutations on the properties of the molecule were determined by comparing the activities of these mutants in the antiviral, antiproliferation and binding assays to the activity observed for his tagged-wild-type interferon-beta-1a. In so doing, we assume that variations in the activities of mutants A1–E, compared to his tagged-wild-type interferon-beta-1a, are qualitatively and quantitatively about the same as the effects that these same mutations would have in the absence of the N-terminal his tag. The equivalent assumption for tagged or fusion constructs of other soluble cytokines is commonly held to be true by practitioners of the technique of alanine scanning mutagenesis, especially when the in vitro functional activity of the tagged or fusion construct is close to that of the wild-type cytokine as is the case here. See, for example, Pearce K. H. Jr, et al., *J. Biol. Chem.* 272:20595–20602 (1997) and Jones J. T., et al., *J. Biol. Chem.* 273:11667–11674 (1998)

The data shown in FIGS. 1–4 suggests three types of effects that were caused by the targeted mutagenesis. These effects may be advantageous for interferon drug development under certain circumstances. The three types of effect are as follows: (a) mutants with higher antiviral activity than that of wild-type interferon-beta-1a (e.g. mutant C1); (b) mutants which display activity in both antiviral and antiproliferation assays, but for which antiproliferation activity is disproportionately low with respect to antiviral activity, compared to wild-type interferon-beta-1a (e.g., mutants C1, D and DE1); and (c) functional antagonists (e.g., A1, B2, CD2 and DE1), which show antiviral and antiproliferative activities that are disproportionately low with respect to receptor binding, compared to wild-type interferon-beta-1a. It can be seen that some mutants fall into more than one class. These classes are reviewed below. While we have characterized these classes of mutants with respect to those examples listed, it should be appreciated that other mutations in these regions may result in similar, or even enhanced effects on activity:

(a) Mutant C1 possesses antiviral activity that is approximately 6-fold greater than that of wild-type his tagged-interferon-beta-1a. This mutant and others of this type are predicted to be useful in reducing the amount of interferon-beta that must be administered to achieve a given level of antiviral effect. Lowering the amount of administered protein is expected to reduce the immunogenicity of the protein and may also reduce side-effects from non-mechanism-based toxicities. Mutations in this class are predicted to be advantageous in situations where the therapeutic benefit of interferon-beta administration results from its antiviral effects, and where antiproliferative effects contribute to toxicity or to unwanted side-effects.

(b) The relative activities (% wild type) of the alanine substituted mutants in antiviral and antiproliferation assay are compared in FIG. 5. Coordinately changed activities (i.e. antiviral and antiproliferation activities that differ by the same factor from the activities of the wild-type his tagged-interferon-beta-1a) are seen in most mutants (those lying on the diagonal line). However, several mutants show greater alterations in activity in one assay relative to the other, compared to wild-type his tagged-interferon-beta-1a, as evidenced by displacement from the diagonal. Three such mutants are shown in the Table 3 below. Mutant C1 shows antiviral activity that is ~6-fold higher than that of wild-type his tagged-interferon-beta-1a, but its activity in the antiproliferation assay is similar to that of wild-type. Mutant C1 thus has antiviral activity that is enhanced by a factor of 5.2 over its antiproliferation activity, relative to wild-type his tagged-interferon-beta-1a. Similarly, mutant D displays 65% of wild type activity in the antiviral assay, but only 20% of wild-type activity in the antiproliferation assay, and thus has antiviral activity that is enhanced 3.4-fold over its antiproliferation activity compared to wild type. Mutant DE1 displays 26% of wild type activity in the antiviral assay but only 8.5% in the antiproliferation assay, and thus has antiviral activity that is enhanced 3.0-fold over its antiproliferation activity compared to wild-type his tagged-interferon-beta-1a. When administered at a concentration sufficient to achieve a desired level of antiviral activity, these mutant proteins will show substantially lower levels of antiproliferative activity than the wild-type protein. Mutations in this class, like those in class (a), are predicted to be advantageous in situations where the therapeutic benefit of interferon-beta administration results from its antiviral effects, and where antiproliferative effects contribute to toxicity or to unwanted side-effects.

TABLE 3

| Mutant | Antiviral Activity (AV) (% wild type) | Antiproliferative (AP) Activity (% wild type) | AV/AP |
|---|---|---|---|
| C1 | 571 | 109 | 5.2 |
| D | 65 | 19 | 3.4 |
| DE1 | 26 | 8.5 | 3.0 |

(c) Mutants with antiviral and antiproliferative activities that are low with respect to receptor binding, as compared to wild-type his tagged-interferon-beta-1a (see Table 4 below). Mutant A1 displays antiviral and antiproliferative activities that are 2.0-fold and 1.8-fold higher than that observed for wild-type his tagged-interferon-beta-1a, but binds to the cognate receptor on Daudi cells with an affinity that is 29-fold higher than wild-type. The binding of this mutant to the IFN-beta receptor is thus enhanced approximately 15-fold compared to the antiviral and antproliferation activities of the protein. Similarly, mutants B2, CD2 and DE1 show enhancements of binding over antiviral activity of 4.6-, 4.6- and 18-fold, respectively, and over antiproliferation activity of 3.5-, 15- and 54-fold. These proteins are predicted to be useful as functional antagonists of the activity of endogenous IFN-beta, and possibly of other endogenous Type I interferons, because they have the ability to bind to and occupy the receptor, and yet generate only a small fraction of the functional response in the target cells that would be seen with wild type IFN-beta.

TABLE 4

| Mutant | Antiviral Activity (AV) (% wt) | Antiproliferative Activity (AP) (% wt) | Cell Binding Activity (% wt) | Binding/AV | Binding/AP |
|---|---|---|---|---|---|
| A1 | 200 | 180 | 2900 | 15 | 16 |
| B2 | 7.1 | 9.2 | 33 | 4.6 | 3.5 |
| CD2 | 150 | 46 | 690 | 4.6 | 15 |
| DE1 | 26 | 8.5 | 460 | 18 | 54 |

G. Mutein Relationship to Three Dimensional Structure of Interferon While published crystal structures for a non-glycosylated form of murine interferon beta (T. Senda, S. Saitoh and Y. Mitsui. Refined Crystal Structure of Recombinant Murine Interferon-β at 2.15 Å Resolution. *J. Mol. Biol.* 253: 187–207 (1995)) and for human interferon alpha-2b (R. Radhakrishnan, L. J. Walter, A. Hruza, P. Reichert, P. P Trotta, T. L. Nagabhushan and M. R. Walter. Zinc Mediated Dimer of Human Interferon-α2b Revealed by X-ray Crystallography. *Structure.* 4: 1453–1463 (1996)) had provided models for the polypeptide backbone of human interferon beta, we have recently solved the structure for interferon-beta-1a in its glycosylated state (M. Karpusas, M. Nolte, C. B. Benton, W. Meier, W. N. Lipscomb, and S. E Goelz. The Crystal Structure of Human Interferon-β at 2.2 Å resolution. *Proc. Natl. Acad. Sci.* USA 94: 11813–11818 (1997)).

The results of our mutational analyses can be summarized with respect to the 3D-structure of interferon-beta-1a (not presented here). Certain mutatations created a reduction in activity (2 to >5 fold reduced). The mutated regions correspond to the substitutions given in Tables 1 and 2. Residues important for antiviral and antiproliferation activity are localized to the lower half of the IFN-beta-1a molecule (Panel a and b). Mutations in the upper half of the molecule, where the amino and carboxy termini are positioned, had no effect on biological activities or receptor binding.

Mutations in the A2 helix, AB, AB2 loop and E helix are most significant in their effect on function and resulted in a dramatic reduction in both activity and cell surface receptor binding. This region (A2 helix, AB& AB2 loop and E helix) corresponds to the IFNAR2 binding site, since none of these mutants bound IFNAR/Fc in our assay.

While those mutations that were important for IFNAR2 binding also affected cell binding, cell surface binding properties are also influenced by residues in other regions of the molecule (B1 helix, C2 helix). It can be seen in the 3-D models (not presented here) depicting the effects of the alanine substitution mutants that the N-terminal, C-terminal and the glycosylated C helix regions of the IFN-beta-1a molecule do not lie within the receptor binding site. Mutations in these regions did not reduce biological activity or reduce cell surface receptor binding.

EXAMPLE 2

Preparation and Characterization of Conjugated Interferon-beta-1a

A. Preparation of PEGylated Interferon.

Nonformulated interferon-beta-1a (sold as AVONEX®) bulk intermediate at 250 Tg/ml in 100 mM sodium phosphate pH 7.2, 200 mM NaCl) was diluted with an equal volume of 100 mM MES pH 5.0 and the pH was adjusted to 5.0 with HCl. The sample was loaded onto an SP-Sepharose® FF column (Pharmacia, Piscataway, N.J.) at 6 mg interferon-beta-1a/ml resin. The column was washed with 5 mM sodium phosphate pH 5.5, 75 mM NaCl, and the product was eluted with 30 mM sodium phosphate pH 6.0, 600 mM NaCl. Elution fractions were analyzed for their absorbance values at 280 nm and the concentration of interferon in the samples estimated from the absorbance using an extinction coefficient of 1.51 for a 1 mg/ml solution.

To a 1 mg/ml solution of the interferon-beta-1a from the SP eluate, 0.5 M sodium phosphate pH 6.0 was added to 50 mM, sodium cyanoborohydride (Aldrich, Milwaukee, Wis.) was added to 5 mM, and 20K PEG aldehyde (Shearwater Polymers, Huntsville, Ala.) was added to 5 mg/ml. The sample was incubated at room temperature for 20 hours. The pegylated interferon was purified from reaction products by sequential chromatography steps on a Superose® 6 FPLC sizing column (Pharmacia) with 5 mM sodium phosphate pH 5.5, 150 mM NaCl as the mobile phase and SP-Sepharose® FF. The sizing column resulted in base line separation of modified and unmodified interferon beta (chromatograph not presented here). The PEG-interferon beta-containing elution pool from gel filtration was diluted 1:1 with water and loaded at 2 mg interferon beta/ml resin onto an SP-Sepharose® column. The column was washed with 5 mM sodium phosphate pH 5.5, 75 mM NaCl and then the pegylated interferon beta was eluted from the column with 5 mM sodium phosphate pH 5.5, 800 mM NaCl. Elution fractions were analyzed for protein content by absorbance at 280 nm. The pegylated interferon concentration is reported in interferon equivalents as the PEG moiety did not contribute to absorbance at 280 nm.

B. Biochemical Characterization of PEGylated Interferon. Samples were analyzed for extent of modification by SDS-PAGE (gel not presented here). Addition of a single PEG resulted in a shift in the apparent mass of interferon from 20 kDa to 55 kDa which was readily apparent upon analysis. In the pegylated sample there was no evidence of unmodified interferon-beta-1a nor of higher mass forms resulting from the presence of additional PEG groups. The presence of a single PEG was verified by MALDI mass spectrometry. The specificity of the pegylation reaction was evaluated by peptide mapping. 20 Tg aliquots of pegylated, and unmodified interferon-beta-1a as a control, in 240 TL of 200 mM Tris HCl pH 9.0, 1 mM EDTA were digested with 1.5 Tg of lysyl endoproteinase from Achromobacter (Wako Bioproducts, Richmond, Va.) for 3–4 hours at 27° C. 200 mg of guanidine HCl was added to each sample and the cleavage products were fractionated on a Vydac $C_4$ column (0.46×25 cm) using a 30 min gradient from 0 to 70% acetonitrile, in 0.1% TFA at a flow rate of 1.4 ml/min. The column effluent was monitored for absorbance at 214 nm.

Results from the analysis are shown in FIG. 6. All of the predicted peptides from the endoproteinase Lys-C digest of interferon-beta-1a have been identified by N-terminal sequencing and mass spectrometry and of these, only the peptide that contains the N-terminus of interferon (AP8) was altered by the modification as evident by its disappearance from the map. The mapping data therefore indicate that the PEG moiety is specifically attached to this peptide. The data further indicate that the PEG modification is targeted at the N-terminus of the protein since only the N-terminal modification would result in the specific loss of this peptide.

Additional evidence for this conclusion was obtained by isolating the PEGylated N-terminal peptide from the endoproteinase Lys-C digest, digesting the peptide further with cyanogen bromide (CNBr) and subjecting this sample to matrix-assisted laser desorption ionization post source decay (MALDI PSD) sequence analysis. CNBr digestion of the N-terminal peptide will further cleave this peptide into two fragments, the terminal methionine (M1) containing the PEG moiety and SYNLLGFLQR (residues 2–11 in the mature interferon beta sequence) Sequence analysis identified the unmodified peptide SYNLLGFLQR, which was the predicted outcome of this treatment.

The antiviral activity of interferon-beta-1a samples was tested on human lung carcinoma cells (A549 cells) that had been exposed to encephalomyocarditis (EMC) virus using the procedures involving MTT staining outlined above. Briefly, A549 cells were pretreated for 24 hours with interferon-beta-1a or PEG-modified interferon-beta-1a (4000, 2000, 1000, 500, 250, 125, 75, 62.5, 31.25, 50, 33.3, 22.2, 14.8, 9.9, 6.6, 4.39 pg/ml) prior to challenge with virus. The assay was performed using duplicate data points for each interferon-beta-1a concentration. The standard deviations are shown as error bars in FIG. 7. The concentration of interferon-beta-1a (formulated or bulk) which offered 50% viral killing (the "50% cytopathic effect") (50% maximum $OD_{450}$) was about 11 pg/ml and the 50% cytopathic effect for PEG modified interferon-beta-1a was about 11 pg/ml. Thus, PEG conjugation did not alter the antiviral activity of interferon-beta-1a. In this assay, we routinely find that the specific activity of interferon-beta-1a is about 10 times greater than the specific activity of interferon-beta-1b and therefore PEGylated interferon-beta-1a is significantly more active than any interferon-beta-1b product.

Interferon-beta-1a was also PEGylated with a 5K PEG-aldehyde moiety that was purchased from Fluka, Inc. (Cat. No. 75936, Ronkonkoma, N.Y.) following the same protocol described for modification with 20K PEG aldehyde except that the reaction contained 2 mg/ml of the 5K PEG. Modification with the 5K PEG was also highly specific for the N-terminus and did not alter the antiviral activity of interferon-beta-1a. Like the 20K adduct, the 5K PEG inteferon-beta-1a was indistinguishable from the unmodified interferon-beta-1a in the antiviral assay.

EXAMPLE 3

PEGylation Protects Interferon-beta-1a from Stress-induced Aggregation

Aggregation of interferon beta has a deleterious effect on activity. Previously, we have shown that glycosylation has a dramatic effect on stability of interferon-beta-1a versus nonglycosylated forms of interferon beta and inferred that glycosylation contributes to the higher specific activity of interferon-beta-1a (Runkel L. et al, Pharm. Res. 15: 641–649). To investigate whether conjugation with a polyalkylene glycol polymer might further stabilize interferon beta, we subjected the PEGylated interferon-beta-1a to thermal stress using the following protocol:

Thermal denaturation was carried out using a CARY 3 UV-visible spectrophotometer fitted with a computer controlled, thermolectrically heated cuvette holder. Solutions of interferon-beta-1a in 20 mM HEPES pH7.5, 20 mM NaCl were equilibrated at 25° C. in a 1 ml cuvette. The temperature of the cuvette holder was then ramped from 25° C. to 80° C. at a rate of 2° C./min, and the denaturation of the protein followed by continuous monitoring of absorbance at 280 nm. The mid-point of the cooperative unfolding event, Tm, was obtained from the melting curves by determining the temperature at which the measured absorbance was mid-way between the values defined by lines extrapolated from the linear regions on each side of the cooperative unfolding transitions.

Results from this analysis are shown in FIG. 8. Whereas the non-PEGylated-interferon-beta-1a denatured and aggregated with a 50% point of transition at 60° C., there was no evidence of aggregation of the PEGylated interferon even at 80° C. In an independent analysis, we extended the thermal stress treatment to 95° C. and even at this more elevated temperature, we saw no evidence for aggregation. Thus, conjugation with this polyethylene glycol polymer has a profound and beneficial effect on the stability of the protein. Similar stabilization was seen with modified interferon-beta-1a containing the 20K and 5K PEG.

EXAMPLE 4

Measurement of Interferon-beta-1a Antiviral Activity in the Plasma of Mice Treated with Interferon-beta-1a and PEGylated Interferon-beta-1a Mice (C57Bl/6) are injected i.v. through the tail vein with either 50,000 Units of interferon-beta-1a or 50,000 Units of PEGylated interferon-beta-1a containing the 20K PEG or an equal volume of phosphate buffer given as a control. Blood from these mice is obtained via retro-orbital bleeds at different time points after injection (immediately, 0.25, 1, 4, 24 and 48 hours). There are at least 3 mice bled at each time point. Whole blood is collected into tubes containing anticoagulant, cells are removed and the resulting plasma frozen until the time of assay. These plasma samples are then tested in anti-viral assays.

The plasma samples are diluted 1:10 into serum free media and passed through a 0.2 um syringe filter. Diluted samples are tested in antiviral assays. Samples are titrated into designated wells of a 96 well tissue culture plate containing A549 cells. Dilutions of a standard interferon-beta-1a (10, 6.7, 4.4, 2.9, 1.3, 0.9 and 0.6 U/ml) and of four plasma samples were assayed on every plate. The A549 cells are pretreated with diluted plasma samples for 24 hours prior to challenge with EMC virus. Following a two-day incubation with virus, viable cells are stained with a solution of MTT (at 5 mg/ml in phosphate buffer) for 1 hour, washed with phosphate buffer, and solubilized with 1.2 N HCl in isopropanol. The wells were read at 450 nm. Standard curves are generated for each plate and used to determine the amount of interferon-beta-1a activity in each test sample. The activity in the samples from the different mice are graphed against the time points in FIG. 9.

The slower loss of PEGylated interferon-beta-1a from circulation as a function of time indicates that the half life of the PEGylated sample is much longer than that of the untreated interferon-beta-1a control. Whereas the control was largely cleared after 4 h, a significant fraction of the PEGylated product was detected after 48 h. Based on the initial levels of activity in serum and those remaining after 48 h, we infer that the half life of the PEGylated interferon is extended when compared to the half life of unmodified interferon-beta-1a. A second highly significant finding from the study was that very little of the PEGylated form was lost during the distribution phase, as evidenced by the similar high levels of activity at time 0 and after 60 min. The data indicate that, unlike the control interferon-beta-1a, the distribution of the PEGylated product is largely limited to the vasculature.

EXAMPLE 5

Comparative Pharmacokinetics and Pharmacodynamics in Primates General Protocols

Comparative studies are conducted with polymer-interferon-beta 1a conjugates and native interferon-beta 1a (as non formulated bulk intermediate interferon-beta-1a in sodium phosphate, and NaCl, pH 7.2) to determine their relative stability and activity in primates. In these studies, the pharmacokinetics and pharmacodynamics of the polymer-interferon-beta-1a conjugate in primates is compared to that of native interferon-beta 1a and reasonable inferences can be extended to humans.

Animals and Methods
Study Design

This is a parallel group, repeat dose study to evaluate the comparative pharmacokinetics and pharmacodynamics of conjugated and unconjugated interferon-beta-1a.

Healthy primates (preferably rhesus monkeys) are used for this study. Prior to dosing, all animals will be evaluated for signs of ill health by a Lab Animal Veterinary on two occasions within 14 days prior to test article administration; one evaluation must be within 24 hours prior to the first test article administration. Only healthy animals will receive the test article. Evaluations will include a general physical examination and pre-dose blood draws for baseline clinical pathology and baseline antibody level to interferon-beta-1a. All animals will be weighed and body temperatures will be recorded within 24 hours prior to test article administrations.

Twelve subjects are enrolled and assigned to groups to receive 1 MU/kg of interferon-beta-1a as either a PEG-interferon-beta-1a conjugate or non-conjugated, but otherwise identical interferon-beta-1a. Administration is by either the subcutaneous (SC) or intravenous (IV) routes. All animals must be naive to interferon-beta treatment. Each animal will be dosed on two occasions; doses will be separated by four weeks. The dose volume will be 1.0 mL/kg.

Blood is drawn for pharmacokinetic testing at various time intervals following each injection. Blood samples for measurements of the interferon induced biological response marker, serum neopterin, are also drawn following administration of study drug.

Evaluations during the study period include clinical observations performed 30 minutes and 1 hour post-dose for signs of toxicitiy. Daily cageside observations will be performed and general appearance, signs of toxicity, discomfort, and changes in behavior will be recorded. Body weights and body temperatures will be recorded at regular intervals through 21 days post-dose.

Assay Methods

Levels of interferon beta in serum are quantitated using a cytopathic effect (CPE) bioassay. The CPE assay measures levels of interferon-mediated antiviral activity. The level of antiviral activity in a sample reflects the number of molecules of active interferon contained in that sample at the time the blood is drawn. This approach has been the standard method to assess the pharmacokinetics of interferon beta. The CPE assay used in the current study detects the ability of interferon beta to protect human lung carcinoma cells (A549, #CCL-185, ATCC, Rockville, Md.) from cytotoxicity due to encephalomyocarditis (EMC) virus. The cells are preincubated for 15 to 20 hours with serum samples to allow the induction and synthesis of interferon inducible proteins that then mount an antiviral response. Afterwards EMC virus is added and incubated for a further 30 hours before assessment of cytotoxicity is made using a crystal violet stain. An internal interferon beta standard as well as PEG conjugate internal standard is tested concurrently with samples on each assay plate. This standard is calibrated against a natural human fibroblast interferon reference standard (WHO Second International Standard for Interferon, Human Fibroblast, Gb-23-902-53). Each assay plate also includes cell growth control wells containing neither interferon beta of any kind nor EMC, and virus control wells contain cells and EMC but no interferon beta. Control plates containing the standard and samples are also prepared to determine the effect, if any, of the samples on cell growth. These plates are stained without the addition of virus.

Samples and standards are tested in duplicate on each of two replicate assay plates, yielding four data points per sample. The geometric mean concentration of the four replicates is reported. The limit of detection in this assay is 10 units (U)/ml.

Serum concentrations of neopterin are determined at the clinical pharmacology unit using commercially available assays.

Pharmacokinetic and Statistical Methods

RstripTM software (MicroMath, Inc., Salt Lake City, Utah) is used to fit data to pharmacokinetic models. Geometric mean concentrations are plotted by time for each group. Since assay results are expressed in dilutions, geometric means are considered more appropriate than arithmetic means. Serum interferon levels are adjusted for baseline values and non-detectable serum concentrations are set to 5 U/ml, which represents one-half the lower limit of detection.

For IV infusion data, a two compartment IV infusion model is fit to the detectable serum concentrations for each subject, and the SC data are fit to a two compartment injection model.

The following pharmacokinetic parameters are calculated:

(i) observed peak concentration, $C_{max}$ (U/ml);

(ii) area under the curve from 0 to 48 hours, AUC using the trapezoidal rule;

(iii) elimination half-life;

and, from IV infusion data (if IV is employed):

(iv) distribution half-life (h);

(v) clearance (ml/h)

(vi) apparent volume of distribution, Vd (L).

WinNonlin (Scientific Consulting Inc., Apex, N.C.) software is used to calculate the elimination half-lives after SC and IM injection.

For neopterin, arithmetic means by time are presented for each group. $E_{max}$, the maximum change from baseline, is calculated. $C_{max}$, AUC and $E_{max}$ are submitted to a one-way analysis of variance to compare dosing groups. $C_{max}$ and AUC are logarithmically transformed prior to analysis; geometric means are reported.

EXAMPLE 6

Comparative Evaluation of PEGylated Interferon beta-1a and Interferon-beta-1a Pharmacokinetics in Rhesus Monkeys Materials and Methods Interferon beta-1a or PEGylated IFN beta-1a were administered to rhesus monkeys on day 1 and again on day 29 by the intravenous (IV) or subcutaneous (SC) routes as described in the general protocol of Example 5. On day 1, six monkeys received IFN beta-1a (3 per route) and another six monkeys received PEGylated IFN beta-1a (3 per route). On day 29, the doses were repeated. The IV dose was administered as a slow bolus injection into a cephalic or saphenous vein.

The SC dose was administered under the skin on the back after shaving the injection site. Blood was collected via the femoral vein at specified time points and allowed to clot to obtain serum. Serum was analyzed for levels of functional drug substances using a validated antiviral CPE method and for serum neopterin and beta2-microglobulin levels as pharmacodynamic measures of activity. Pharmacological parameters were calculated using WinNonlin version 2.0 software (Scientific Consulting Inc., Apex, N.C.).

The concentration data were analyzed by standard model-independent methods (noncompartmental analysis) to obtain pharmacokinetic parameters. Area under the curve (AUC) was calculated using the trapezoidal rule. Statistical analyses, including arithmetic mean and standard deviation, were performed using Microsoft Excel version 5.0 software (Microsoft Corp., Redmond Wash.). Concentration values reported as below limits of quantitation (BLQ) were not used in the pharmacokinetic analysis. Due to the fact that different computers and computer programs round off or truncate numbers differently, values in some tables (e.g. means, standard deviations, or individual values) may differ slightly from those in other tables, from individually calculated data, or from statistical analysis data. Neither the integrity nor interpretation of the data was affected by these differences.

Results and Discussion

Within each route of administration, pegylated IFN beta-1a exhibited higher bioavailability (as measured by the area under the serum concentration-time curve). In addition the pegylated IFN beta-1a had a higher absolute bioavailability as compared to IFN beta-1a when administered by the SC route. We summarize the pharmacokinetic parameters in Table 5. Administration of pegylated IFN beta-1a by both IV and SC routes results in an increase in the half-life as well as the AUC of IFN beta-1a.

TABLE 5

Mean (±Std. Dev.) BG9418 Pharmacokinetic Parameters Following IV or SC (Dose 1) Administration of 1 MU/kg of IFN b-1a or Pegylated IFN B-1a to Rhesus Monkeys[a]

| Formulation (Route of Administration) | $C_{max}$ | $T_{max}$ | AUC U*hr/mL | CL (mL/kg) | Vss (mL/kg) | $T_{1/2}$ |
|---|---|---|---|---|---|---|
| IFN B-1a (IV) | 6400 (±) | 0.083 (±0) | 4453 (±799) | 229 (±38) | 543 (±147) | 3.2 (±1.4) |
| Pegylated IFN-b-1a (IV) | 10800 (±3811) | 0.083 (±0) | 34373 (±3601) | 29 (±3) | 250 (±30) | 9.5 (±2.1) |
| IFN B-1a (SC) | 277 (±75) | 5.3 (±1.2) | 4753 (±3170) | N/A | N/A | 10.0 (±2.9) |
| Pegylated IFN B-1a (SC) | 1080 (±381) | 3.3 (±1.2) | 42283 (±5934) | N/A | N/A | 22.0 (±3.4) |

[a] n = 3

Following IV administration of the first dose, the mean (±std. dev.) peak serum concentrations (Cmax) of IFN beta-1a and pegylated IFN beta-1a were 6400 (±0) and 10800 (±3.5) U/mL, respectively. The mean (±std. dev.) AUC values were 4453 (±799) and 34373 (±3601) U*hr/mL, respectively. Following the first SC administration, the mean (±std. dev.) Cmax of IFN beta-1a and pegylated IFN beta-1a were 277 (±75) and 1080 (±381) U/mL, respectively. Mean (±std. dev.) AUC values were 4753 (±3170) and 44952 (±1443) U*hr/mL, respectively.

Both serum neopterin and serum beta2microglobulin levels were elevated after treatment with IFN-beta and pegylated IFN-beta, indicating pharmacologic activity of the products. At the high doses of test compounds used, there was no difference in the pharmacologic activity of IFN beta-1a and pegylated IFN beta-1a by either route of administration (data now shown).

EXAMPLE 7

Comparative Evaluation of Pegylated Interferon beta-1a and Interferon-beta-1a Pharmacokinetics in Rats Following Various Modes of Administration The purpose of this study was to determine the comparative bioavailability of interferon beta-1a and pegylated interferon beta-1a by several routes of administration.

Materials and Methods:

We used female Lewis rats (at 190 grams each) for pharmacokinetic analyses with two rats per route/formulation. The rats were jugular cannulated and either human interferon beta-1a or 5K pegylated human interferon beta-1a or 20K human interferon beta-1a (in a vehicle consisting of 14 mg/ml HSA in 50 mM sodium phosphate, 100 mM NaCl, pH 7.2) were administered intravenously, intraperitoneally, orally, subcutaneously or intratracheally. Blood was processed several times over a 72 hour period at 0, 5 min, 15 min, 30 min, 75 min, 3 hr, 24 h, 48 h and 72 h. The protocol is presented in Table 6. The cytopathic effect (CPE) bioassay was run on the serum samples to detect interferon-beta in the serum. The results generated with unmodified interferon beta-1a and interferon beta-1a pegylated with 20K PEG are presented in Table 7. In all cases, pegylation resulted in significant increases in t½ and AUC.

TABLE 6

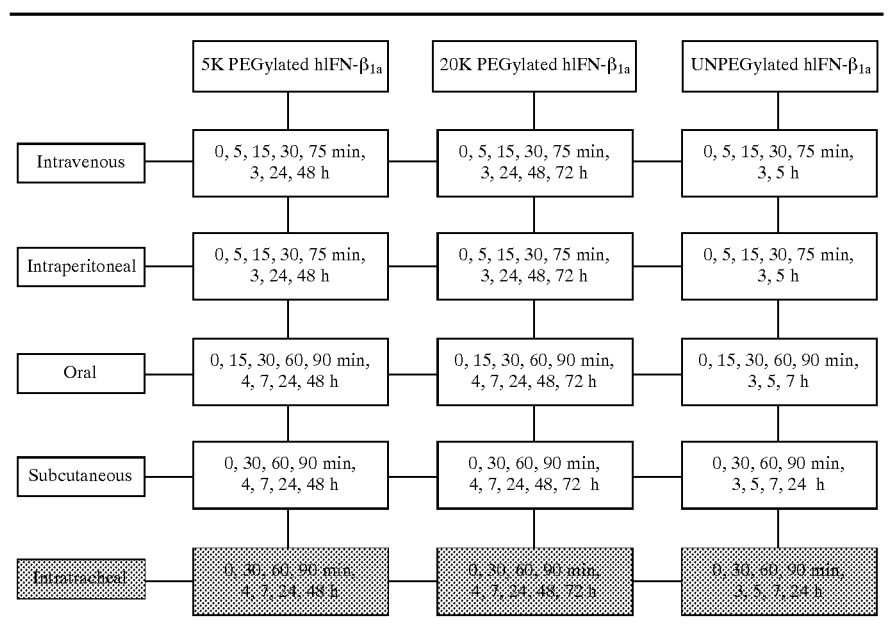

TABLE 7

Pharmacokinetic parameters following IV, SC, IP or IT administration of Interferon beta-1a (IFN) and pegylated IFN-beta 1a (IFN-PEG) in Rats

| Formulation (Route of Administration) | $C_{max}$ (U/mL) | $T_{max}$ (hr) | AUC/Dose (U hr)/(mL ug) | $T_{½}$ (hr) |
|---|---|---|---|---|
| IFN (IV, 20 ug does) | 64000 | 0.25 | 3035 | 1.25 |
| IFN-PEG (IV, 3 ug dose) | 23970 | 0.08 | 47728 | 8.44 |
| IFN (SC, 20 ug dose) | 2400 | 1.00 | 464.4 | 0.96 |
| UFN-PEG (SC, 3 ug dose) | 2400 | 7.00 | 14688 | 11.9 |
| IFN (IP, 20 ug dose) | 26000 | 1.25 | 4159 | 1.53 |
| IFN-PEG (IP, 3 ug dose) | 9700 | 1.25 | 52148 | 16.2 |
| IFN (IT, 15 ug dose) | 240 | 1.5 | 70.7 | 1.29 |
| IFN-PEG (IT, 15 ug dose) | 270 | 7.0 | 233.5 | 6.21 |

EXAMPLE 8

Anti-Angiogenic Effects of Polymer-Conjugated Interferon Beta-1a Assessment of the Ability of PEGylated Interferon-beta-1a to Inhibit Endothelial Cell Proliferation In Vitro Human venous endothelial cells (Cell Systems, Cat. #2V0-P75) and human dermal microvascular endothelial cells (Cell Systems, Cat. # 2M1-C25) are maintained in culture with CS-C Medium Kit (Cell Systems, Cat. # 4Z0-500). Twenty-four hours prior to the experiment, cells are trypsinized, and resuspended in assay medium, 90% M199 and 10% fetal bovine serum (FBS), and are adjusted to desired cell density. Cells are then plated onto gelatin-coated 24 or 96 well plates, either at 12,500 cells/well or 2,000 cells/well, respectively.

After overnight incubation, the assay medium is replaced with fresh medium containing 20 ng/ml of human recombinant basic Fibroblast Growth Factor (Becton Dickinson, Cat. # 40060) and various concentrations of conjugated and unconjugated interferon-beta-1a proteins or positive control (endostatin can be used as a positive control, as could an antibody to bFGF). The final volume is adjusted to 0.5 ml in the 24 well plate or 0.2 ml in the 96 well plate.

After seventy-two hours, cells are trypsinized for Coulter counting, frozen for CyQuant fluorescense reading, or labeled with [3H] thymidine. The inhibition of endothelial cell proliferation in vitro by conjugated and unconjugated interferon-beta 1a was comparable, indicating that PEGylation had not interfered with the ability of the interferon to function in this setting.

This in vitro assay tests the human interferon-beta molecules of the invention for effects on endothelial cell proliferation which may be indicative of anti-angiogenic effects in vivo. See O'Reilly, M. S., T. Boehm, Y. Shing, N. Fukal, G. Vasios, W. Lane, E. Flynn, J. Birkhead, B. Olsen, and J. Folkman. (1997). Endostatin: An Endogenous Inhibitor of Angiogensis and Tumor Growth. *Cell* 88, 277–285.

EXAMPLE 9

In Vivo Model to Test Anti-Angiogenic and Neovascularization Effects of Conjugated Interferon-beta-1a A variety of models have been developed to test for the anti-angiogenic and anti-neovascularization effects of the molecules described herein. Some of these models have been described in U.S. Pat. No. 5,733,876 (Mar. 31,1998: "Method of inhibiting angiogenesis) and U.S. Pat. No. 5,135,919 (Aug. 4, 1992:"Method and a pharmaceutical composition for the inhibition of angiogenesis"). Other assays include the shell-less chorioallantoic membrane (CAM) assay of S. Taylor and J. Folkman; Nature, 297, 307 (1982) and R. Crum. S. Szabo and J. Folkman; Science. 230. 1375 (1985); the mouse dorsal air sac method antigiogenesis model of Folkman, J. et al.; J. Exp. Med., 133, 275 (1971) and the rat corneal micropocket assay of Gimbrone, M. A. Jr. et al., J. Natl. Cancer Inst. 52, 413(1974) in which corneal vascularization is induced in adult male rats of the Sprague-Dawley strain (Charles River, Japan) by implanting 500 ng of basic FGF (bovine, R & D Systems, Inc.) impregnated in EVA (ethylene-vinyl acetate copolymer) pellets in each cornea.

Other methods for testing PEGylated murine interferon-beta for anti-angiogenic effects in an animal model include (but are not limited to) protocols for screening new potential anticancer agents as described in the original Cancer Chemotherapy Reports, Part 3, Vol. 3, No. 2, September 1972 and the supplement In Vivo Cancer Models, 1976–1982, NIH Publication No. 84-2635, February 1984.

Because of the species barriers of Type I interferons, to assess the anti-angiogenic activity of polymer conjugated interferon-beta in rodent models, polymer conjugated rodent interferon-beta preparations are generated. Such screeing methods are exemplified by a protocol to test for the anti-angiogenic effects of pegylated murine interferon-beta on subcutaneously-implanted Lewis Lung Carcinoma.

Origin of Tumor Line:

Arose spontaeously in 1951 as a carcinoma of the lung in a C57BL/6 mouse.

Summary of Test Procedures: A tumor fragment is implanted subcutaneously in the axillary region of a B6D2F1 mouse. The test agent (i.e, a PEGylated interferon of the invention) is administered at various doses, subcutaneously (SC) or intraperitoneally (IP) on multiple days following tumor implantation. The parameter measured is median survival time. Results are expressed as a percentage of control survival time.

Animals:

Propagation: C57BL/6 mice.

Testing: B6D2F1 mice.

Weight: Mice should be within a 3 gm weight range with a minimum weight of 18 gm for males and 17 gm for females.

Sex: One sex is used for all test and control animals in one experiment.

Source: One source, if feasible, for all animals in one experiment.

Experiment Size:

Ten animals per test group.

Tumor Transfer:

PROPAGATION:

Fragment: Prepare a 2–4 mm fragment of a s.c. donor tumor

Time: Day 13–15

Site: Implant the fragment s.c. in the axillary region with a puncture in the inguinal region.

TESTING:

Fragment: Prepare a 2–4 mm fragment of s.c. donor tumor.

Time: Day 13–15.

Site: Implant the fragment s.c. in the axillary region with a puncture in the inguinal region.

Testing Schedule:

Day 0: Implant tumor. Run bacterial cultures. Test positive control compound in every odd-numbered experiment. Prepare materials. Record deaths daily.

Day 1: Check cultures. Discard experiment if contaminated. Randomize animals. Treat as instructed (on day 1 and on following days).

Day 2: Recheck cultures. Discard experiment if contaminated.

Day 5: Weigh Day 2 and day of initial test agent toxicity evaluation.

Day 14: Control early-death day.

Day 48: Control no-take day.

Day 60: End and evaluate experiment. Examine lungs grossly for tumor.

Quality Control:

Schedule the positive control compound (NSC26271 (Cytoxan at a dose of 100 mg/kg/injection)) in every odd-numbered experiment, the regimen for which is intraperitoneal on Day 1 only. The lower Test/Control limit for the positive control is 140%. The acceptable untreated control median survival time is 19–35.6 days.

Evaluation:

The parameter measured is median survival time Compute mean animal body weights for Day 1 and Day 5, compute Test/Control ratio for all test groups with. The mean animal body weights for staging day and final evaluation day are computed. The Test/Control ratio is computed for all test groups with >65% survivors on Day 5. A Test/Control ratio value <86% indicates toxicity. An excessive body weight change difference (test minus control) may also be used in evaluating toxicity.

Criteria for Activity:

An initial Test/Control ratio greater than or equal to 140% is considered necessary to demonstrate moderate activity. A reproducible Test/Control ratio value of greater than or equal to 150% is considered significant activity.

What is claimed is:

1. A composition comprising the glycosylated interferon-beta-1a of SEQ ID NO: 25 coupled to a non-naturally-occurring polymer at an N-terminal end of said glycosylated interferon-beta-1a, said polymer comprising a polyalkylene glycol moiety.

2. The composition of claim 1, wherein the polyalkylene moiety is coupled to the interferon-beta by way of a group selected from an aldehyde group, a maleimide group, a vinylsulfone group, a haloacetate group, plurality of histidine residues, a hydrazine group and an aminothiol group.

3. The composition of claim 1, wherein the interferon-beta-1a of SEQ ID NO: 25 is an inlerferon-beta-1a fusion protein.

4. The composition of claim 3, wherein the interferon-beta-1a fusion protein comprises a portion of an immunoglobulin molecule.

5. A composition comprising the glycosylated interferon-beta-1a of SEQ ED NO: 26 coupled to a non-naturally-occurring polymer at the N-terminus of said glycosylated interferon-beta-1a, said polymer comprising a polyalkylene glycol moiety.

6. The composition of claim 5, wherein the glycosylated interferon-beta-1a of SEQ ID NO: 26 is an interferon-beta-1a fusion protein.

7. The composition of claim 6, wherein the interferon-beta-1a fusion protein comprises a portion of an immunoglobulin molecule.

8. A physiologically active interferon-beta composition comprising a physiologically active interferon-beta-1a comprising the amino acid sequence of SEQ ID NO: 25 coupled to a polymer comprising a polyalkylene glycol moiety, wherein the interferon-beta-1a is coupled to the polymer at a site on the interferon-beta-1a that is an N- terminal end, wherein the physiologically active interferon-beta 1a and the polyalkylene glycol moiety are arranged such that the physiologically active interferon-beta-1a in the physiologically active interferon-beta composition has an activity at least 2-fold greater relative to physiologically active interferon-beta-1b, when measured by an antiviral assay.

9. The composition of claim 8, wherein the interferon-beta-1a is coupled to the polymer at a site by way of a glycan moiety the interferon-beta-1a.

10. The composition of claim 8, wherein interferon-beta-1a is an interferon-beta-1a fusion protein.

11. The composition of claim 10, wherein the interferon-beta-1a fusion protein comprises a portion of an immunoglobulin molecule.

12. A physiologically active interferon-beta composition comprising a pysiologically active glycosylated interferon-beta-1a comprising the amino acid sequence of SEQ ID NO:

25 N-terminally coupled to a polymer comprising a polyalkylene glycol moiety. wherein the physiologically active interferon-beta-1a and the polyalkylene glycol moiety are arranged such that the physiologically active interferon-beta-1a in the physiologically active interferon-beta composition has equal activity relative to physiologically active interferon-beta lacking said moiety, when measured by an antiviral assay.

13. The composition of claim 12, wherein the interferon-beta is coupled to the polymer at a site by way of a glycan moiety on the interferon-beta.

14. The composition of claim 12, wherein the interferon-beta-1a is an interferon beta fusion protein.

15. The composition of claim 14, wherein the interferon beta fusion protein comprises a portion of an immunoglobulin molecule.

16. A stable, aqueously soluble, conjugated interferon-beta-1a complex comprising a interferon-beta-1a comprising the amino acid sequence of SEQ ID NO: 25 N-terminally coupled to a polyethylene glycol moiety, wherein the interferon-beta-1a is coupled to the polyethylene glycol moiety by a labile bond, wherein the labile bond is cleavable by biochemical hydrolysis and/or proteolysis.

17. A interferon-beta composition according to claims 12, or 16, wherein the polymer has a molecular weight of from about 5 to about 40 kilodaltons.

18. A pharmaceutical composition comprising the interferon-beta composition of claim 17.

19. A physiologically active interferon-beta composition comprising a physiologically active interferon-beta-1a comprising the amino acid sequence of SEQ ID NO:26 coupled to a non-naturally-occurring polymer at the N-terminus of said glycosylated interferon-beta-1a, said polymer comprising a polyalkylene glycol moiety wherein the physiologically active interferon-beta-1a and the polyalkylene glycol moiety are arranged such that the physiologically active interferon-beta-1a in the physiologically active interferon-beta composition has an activity at least 2-fold greater relative to physiologically active interferon-beta-1b, when measured by an antiviral assay.

20. The composition of claim 19, wherein the interferon-beta-1a is an interferon-beta-1a fusion protein.

21. The composition of claim 20, wherein the interferon-beta-1a fusion protein comprises a portion of an immunoglobulin molecule.

22. A physiologically active interferon-beta composition comprising a physiologically active glycosylated interferon-beta-1a, comprising the amino acid sequence of SEQ ID NO: 25, N-terminally coupled to a polymer comprising a polyalkylene glycol moiety, wherein the physiologically active interferon-beta-1a and the polyalkylene glycol moiety are arranged such that the physiologically active interferon-beta-1a in the physiologically active interferon-beta composition has equal activity relative to physiologicaily active interferon-beta lacking said moiety, when measured by an antiviral assay.

23. The composition of claim 22, wherein the interferon-beta-1a is an interferon beta fusion protein.

24. The composition of claim 23, wherein the interferon beta fusion protein comprises a portion of an immunoglobulin molecule.

* * * * *

UNITED STATES PATENT AND TRADEMARK OFFICE
CERTIFICATE OF CORRECTION

PATENT NO. : 6,962,978 B2  
APPLICATION NO. : 09/832658  
DATED : November 8, 2005  
INVENTOR(S) : Pepinsky et al.

Page 1 of 1

It is certified that error appears in the above-identified patent and that said Letters Patent is hereby corrected as shown below:

Column 53, line 55 Claim 3, the text "is an inlerferon-beta-1a" should read -- is an interferon-beta-1a --.

Column 53, line 61 Claim 5, the text "SEQ ED NO: 26" should read -- SEQ ID NO: 26 --.

Column 54, line 59 Claim 9, the text "moiety the interferon-beta-1a fusion protein" should read -- moiety of the interferon-beta-1a fusion protein --.

Column 54, line 66 Claim 12, the text "comprising a pysiologically active glycosylated interferon-beta-1a" should read -- comprising a physiologically active glycosylated interferon-beta-1a --.

Column 55, line 2 Claim 12, the text "alkylene glycol moiety wherein the physiologically active" should read -- alkylene glycol moiety, wherein the physiologically active --.

Signed and Sealed this

Seventeenth Day of February, 2009

JOHN DOLL  
*Acting Director of the United States Patent and Trademark Office*